United States Patent [19]  
Soma et al.

[11] 4,097,587  
[45] Jun. 27, 1978

[54] 1,3,8-TRIAZASPIRO[4.5]DECANE-2,4-DIONE POLYMER STABILIZERS

[75] Inventors: Nobuo Soma; Tomoyuki Kurumada, both of Tokyo, Japan; Heimo Brunetti, Reinach; Jean Rody, Basel, both of Switzerland

[73] Assignees: Sankyo Company, Limited, Tokyo, Japan; CIBA-GEIGY Corporation, Ardsley, N.Y.

[21] Appl. No.: 687,794

[22] Filed: May 19, 1976

[30] Foreign Application Priority Data

May 28, 1975  Japan .................................. 50-63851

[51] Int. Cl.$^2$ ...................... C07D 471/10; C08K 5/34
[52] U.S. Cl. ......................... 260/45.8 A; 260/293.63; 260/293.64; 260/293.66; 260/45.8 N
[58] Field of Search ...................... 260/293.63, 293.64, 260/293.66, 45.8 N, 45.8 A

[56] References Cited

U.S. PATENT DOCUMENTS

| | | | |
|---|---|---|---|
| 3,536,722 | 10/1970 | Murayama et al. | 260/293.66 |
| 3,542,729 | 11/1970 | Murayama et al. | 260/293.63 |
| 3,639,409 | 2/1972 | Murayama et al. | 260/293.66 |
| 3,941,744 | 3/1976 | Murayama et al. | 260/293.66 |

OTHER PUBLICATIONS

Mailey et al., "J. Org. Chem." vol. 22, pages 1061–1065, (1957).

*Primary Examiner*—Henry R. Jiles
*Assistant Examiner*—Robert T. Bond
*Attorney, Agent, or Firm*—Vincent J. Cavalieri

[57] ABSTRACT

Novel 7,7,9,9-tetra-substituted-1,3,8-triazaspiro[4.5]decane-2,4-diones having an alkyl or allyl group at either the 6- or the 10- position are useful for the stabilization of polymers against photo- and thermal- deterioration.

14 Claims, No Drawings

1,3,8-TRIAZASPIRO[4.5]DECANE-2,4-DIONE POLYMER STABILIZERS

BACKGROUND OF THE INVENTION

The present invention relates to certain novel piperidine derivatives, specifically certain novel 7,7,9,9-tetrasubstituted-1,3,8-triazaspiro[4.5]decane-2,4-diones having an alkyl or allyl substituent at the 6- or 10- position, and to their use as polymer stabilizers, and provides processes for their preparation.

Various compounds which may be represented by the general formula:

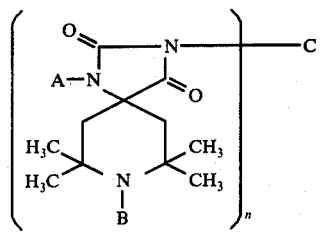

are known as stabilizers for polymeric materials. Thus for example:

U.S. Pat. No. 3,705,126 discloses compounds having this formula wherein A, B and C each represents a hydrogen atom and n = 1;

U.S. Pat. Nos. 3,536,722, 3,547,874 and 3,474,068 disclose compounds of this formula wherein A and C each represents a hydrogen atom, B represents an oxyl radical and n = 1;

U.S. Pat. Nos. 3,542,729 and 3,639,409 and German Offenlegungsschrift No. 2,233,122 disclose compounds of this formula wherein A and B each represents a hydrogen atom, C represents various substituents and n represents an integer depending upon the valency of the substituent C; German Offenlegungsschrift No. 2,326,010 discloses compounds of this formula wherein A and C each represents a hydrogen atom and B represents various different types of substituent; Japanese Patent Publications No. 45-35661 and 46-39105 disclose compounds having this formula wherein A represents a hydrogen atom, B represents an oxyl radical, C represents various types of substituent, and n is an integer depending upon the valency of substituent C; and German Offenlegungsschriften No. 2,227,689 and No. 2,233,121 and Japanese Patent Specification No. 48-81874, as laid open to public inspection, disclose compounds of this formula wherein A represents a hydrogen atom or various types of substituent, B and C each represents various types of substituent and n is an integer depending upon the valency of substituent C.

SUMMARY OF THE INVENTION

It is an object of the present invention to provide novel piperidine derivatives of this type which have an effective and improved stabilization effect for polymeric materials.

It is a further object of the invention to provide a polymer composition containing an effective stabilizing amount of such a piperidine derivative.

The piperidine derivatives of the present invention have the formula (I):

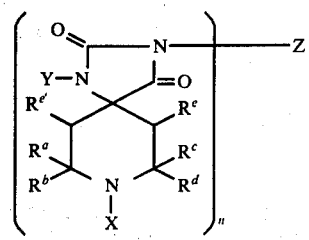

wherein:
$R^a$ represents a methyl group;
$R^b$ represents a lower alkyl group;
$R^c$ represents an alkyl group;
$R^d$ represents an alkyl group, a phenyl group or an aralkyl group;

or $R^c$ and $R^d$, together with the carbon atom to which they are attached, represent a cycloalkyl group;
one of $R^e$ and $R^{e'}$ represents a hydrogen atom and the other of $R^e$ and $R^{e'}$ represents a lower alkyl group or an allyl group;
n is 1 or 2;
Y represents a hydrogen atom or, when neither X nor Z represents a hydrogen atom, Y represents a hydrogen atom, a methyl group, an ethyl group, an allyl group or a benzyl group;
X represents a hydrogen atom, an oxyl radical, a lower alkyl group, an alkenyl group, a benzyl group, a 2,3-epoxypropyl group or a group of formula —$CH_2CH_2OR^1$ (wherein $R^1$ represents a hydrogen atom or an aliphatic, aromatic, aralphatic or alicyclic acyl group);
when n = 1:
Z represents a hydrogen atom, an alkyl group, an alkenyl group, an aralkyl group which is unsubstituted or has one or more substituents in its aryl moiety, an aryl group which is unsubstituted or has one or more chlorine and/or methyl substituents, a cyclohexyl group, a 2,3-epoxypropyl group, an alkoxyalkyl group, a phenoxyalkyl group, a group of formula —$CH_2 \cdot COOR^2$ (wherein $R^2$ represents an alkyl group or a phenyl group) or a group of formula

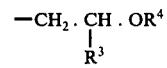

(wherein $R^3$ represents a hydrogen atom, a methyl group or a phenyl group, and $R^4$ represents a hydrogen atom or an aliphatic, aromatic, aralphatic or alicyclic acyl group);
when n = 2:
Z represents an alkylene group, which is optionally interrupted by an oxygen atom, a 2-butenylene group, a xylylene group; an arylene group which is unsubstituted or has one or more methyl substituents, a group of formula

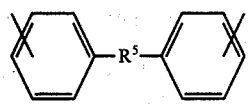

(wherein $R^5$ represents an oxygen atom or a methylene group), a group of formula —$CH_2.COOR^6OCO.CH_2$— (wherein $R^6$ represents an alkylene group) or a group of formula

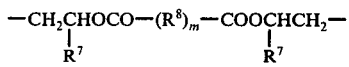

(wherein $R^7$ represents a hydrogen atom, a methyl group or a phenyl group, $m$ is 0 or 1 and $R^8$ represents an alkylene group optionally interrupted by a sulphur atom, an alkenylene group, a phenylene group or a 1,4-cyclohexylene group);
and acid addition salts thereof.

In this Specification, the term "lower alkyl group" means an alkyl group having up to 6 carbon atoms.

In accordance with the invention, it has been discovered that the novel piperidine derivatives of formula (I) or mixtures thereof and/or acid addition salts thereof can effectively stabilize a wide range of polymers against photo- and thermal- deterioration and have superior compatibility with polymers, particularly with olefin polymers. The piperidine derivatives (I) may readily be incorporated into the polymer by conventional techniques at any convenient stage.

DESCRIPTION OF PREFERRED EMBODIMENTS

In formula (I), where $R^b$ represents a lower alkyl group, it may suitably be a lower alkyl group having from 1 to 5 carbon atoms, e.g. a methyl, ethyl, propyl, butyl, pentyl or isopentyl group.

When $R^c$ and/or $R^d$ represents an alkyl group, it may suitably be an alkyl group having from 1 to 9 carbon atoms, e.g. a methyl, ethyl, propyl, butyl, isobutyl, pentyl, isopentyl, hexyl, 3-methylhexyl or nonyl group, most especially an alkyl group having from 1 to 5 carbon atoms. When $R^d$ represents an aralkyl group, it may suitably be a phenylalkyl group having 7 or 8 carbon atoms, e.g. a benzyl or phenethyl group. When $R^c$ and $R^d$, together with the carbon atom to which they are attached, represent a cycloalkyl group, it may be one having from 5 to 7 carbon atoms, e.g. a cyclopentyl, cyclohexyl or cycloheptyl group, most preferably a cyclohexyl group.

When $R^e$ represents a lower alkyl group, it may suitably be one having from 1 to 4 carbon atoms, e.g. a methyl, ethyl, propyl, butyl or isobutyl group.

When X represents a lower alkyl group, it may suitably be one having from 1 to 4 carbon atoms, e.g. a methyl, ethyl, propyl or butyl group, most preferably a methyl group. When X represents an alkenyl group, it may suitably be one having 3 or 4 carbon atoms, e.g. an allyl or 2-butenyl group, most preferably an allyl group. When X represents a group of the formula —$CH_2CH_2OR^1$, $R^1$ represents a hydrogen atom or an aliphatic, aromatic, araliphatic or alicyclic acyl group suitably having up to 18 carbon atoms and preferably a group of formula —$COR^9$ (in which $R^9$ represents: an alkyl group having from 1 to 17 carbon atoms, e.g. a methyl, ethyl, propyl, isopropyl, butyl, heptyl, 1-ethylpentyl, nonyl, undecyl or heptadecyl group; an alkenyl group having from 2 to 4 carbon atoms, e.g. a vinyl, 1-propenyl, isopropenyl, 2-methyl-1-propenyl or 1-butenyl group; a phenyl group which is unsubstituted or has up to 3 chlorine, $C_{1-4}$ alkyl, $C_{1-8}$ alkoxy or hydroxy substituents, the substituents being the same or different, e.g. phenyl itself, o-chlorophenyl, m-chlorophenyl, p-chlorophenyl, 2,4-dichlorophenyl, o-methylphenyl, m-methylphenyl, p-methylphenyl, p-isopropylphenyl, p-t-butylphenyl, p-methoxyphenyl, p-ethoxyphenyl, p-butoxyphenyl, p-octoxyphenyl, 3,4,5-trimethoxyphenyl, o-hydroxyphenyl or 4-hydroxy-3,5-di-t-butylphenyl; an aralkyl group having 7 or 8 carbon atoms which is unsubstituted or has up to 3 chlorine, $C_{1-4}$ alkyl, $C_{1-8}$ alkoxy or hydroxy substituents in its aryl moiety, the substituents being the same or different, e.g. a benzyl, phenethyl, p-methylbenzyl or 4-hydroxy-3,5-di-t-butylphenethyl group; a styryl group; or a cyclohexyl group; most preferably an alkyl group having from 1 to 17 carbon atoms or a phenyl group).

Furthermore, when $n = 1$: Z preferably represents:
an alkyl group having from 1 to 18 carbon atoms, e.g. a methyl, ethyl, propyl, butyl, isopentyl, hexyl, octyl, decyl, dodecyl, hexadecyl or octadecyl group, more preferably an alkyl group having from 1 to 12 and most preferably from 1 to 8 carbon atoms;
an alkenyl group having 3 or 4 carbon atoms, e.g. an allyl, 2-butenyl or 2-methylallyl group, more preferably an allyl group;
a phenylalkyl group having 7 or 8 carbon atoms and which is unsubstituted or which has up to 3 chlorine, $C_{1-4}$ alkyl, $C_{1-8}$ alkoxy or hydroxy substituents in its aryl moiety, the substituents being the same or different, e.g. a benzyl, phenethyl, o-chlorobenzyl, m-chlorobenzyl, p-chlorobenzyl, o-methylbenzyl, m-methylbenzyl, p-methylbenzyl, p-isopropylbenzyl, p-t-butylbenzyl, p-methoxybenzyl, p-butoxybenzyl, p-octoxybenzyl or 4-hydroxy-3,5-di-t-butylbenzyl group, most preferably a benzyl group;
an aryl group having from 6 to 10 carbon atoms and which is unsubstituted or has one or more chlorine and/or methyl substituents, e.g. a phenyl, o-chlorophenyl, m-chlorophenyl, p-chlorophenyl, o-tolyl, m-tolyl, p-tolyl or α-naphthyl group, most preferably a phenyl group; an alkoxyalkyl group having from 2 to 6 carbon atoms, e.g. a methoxymethyl, ethoxymethyl, 2-methoxyethyl, 2-ethoxyethyl or 2-butoxyethyl group, most preferably an alkoxyalkyl group having a total of 3 or 4 carbon atoms; a phenoxyalkyl group having 2 or 3 carbon atoms in its alkyl moiety, e.g. a phenoxyethyl group;
a group of formula —$CH_2.COOR^2$ in which $R^2$ represents an alkyl group having from 1 to 8 carbon atoms, e.g. a methyl, ethyl, isopropyl, butyl, isobutyl, isopentyl or octyl group, or a phenyl group, most preferably an alkyl group having from 1 to 4 carbon atoms;
a group of formula

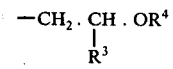

in which $R^3$ is as previously defined and is most preferably a hydrogen atom and $R^4$ is preferably a hydrogen atom or an aliphatic, aromatic, araliphatic or alicyclic acyl group having up to 18 carbon atoms, suitably a group of formula —$COR^{10}$ (in which $R^{10}$ represents: an alkyl group having from 1 to 17 carbon atoms, e.g. a methyl, ethyl, propyl, isopropyl, butyl, pentyl, isopentyl, heptyl, 1-ethylpentyl, nonyl, undecyl or heptadecyl group; an alkenyl group having from 2 to 5 carbon atoms, e.g. a vinyl, 1-propenyl, isopropenyl, 2-methyl-1-propenyl, 1-butenyl or 1,3-pentadienyl group; a phenyl group which is unsubstituted or has up to 3 chlorine, $C_{1-4}$ alkyl, $C_{1-8}$ alkoxy or hydroxy substituents, which substituents may be the same or different, e.g. phenyl itself, o-chlorophenyl, m-chlorophenyl, p-chlorophenyl, 2,4-dichlorophenyl, o-methylphenyl, m-methylphenyl, p-methylphenyl, p-isopropylphenyl, p-t-butylphenyl, m-methoxyphenyl, p-methoxyphenyl, p-ethoxyphenyl, p-butoxyphenyl, p-octoxyphenyl, 3,4,5-trimethoxyphenyl, o-hydroxyphenyl or 4-hydroxy-3,5-di-t-butoxyphenyl; an aralkyl group having 7 or 8 carbon atoms which is unsubstituted or has up to 3 chlorine, $C_{1-4}$ alkyl, $C_{1-8}$ alkoxy or hydroxy substituents in its aryl moiety, the substituents being the same or different, e.g. benzyl, phenethyl, p-methylbenzyl or 4-hydroxy-3,5-di-t-butylphenethyl; a styryl group; or a cyclohexyl group; $R^{10}$ is most preferably an alkyl group having from 1 to 17 carbon atoms, a phenyl group which is unsubstituted or has up to 3 $C_{1-4}$ alkyl and/or hydroxy substituents or a 4-hydroxy-3,5-di-t-butylphenethyl group);

a hydrogen atom; or a 2,3-epoxypropyl group.

Alternatively, when $n = 2$: Z preferably repesents:

an alkylene group having from 1 to 10 carbon atoms, the chain of which may optionally be interrupted by an oxygen atom, e.g. a methylene, ethylene, tetramethylene, hexamethylene, octamethylene, decamethylene or 3-oxapentamethylene ($-CH_2CH_2OCH_2CH_2-$) group, most preferably an alkylene group having from 2 to 6 carbon atoms;

o-xylylene, m-xylylene or p-xylylene, most preferably p-xylylene;

an arylene group having from 6 to 10 carbon atoms, which is unsubstituted or which has one or more methyl substituents, e.g. a m-phenylene, p-phenylene, 2,4-tolylene or 1,5-naphthylene group;

an oxydi-p-phenylene or methylenedi-p-phenylene group;

a group of formula $-CH_2.COOR^6OCO.CH_2-$ in which $R^6$ represents an alkylene group having from 2 to 8 carbon atoms, e.g. an ethylene, tetramethylene, hexamethylene or 2-ethyl-1,3-hexylene group, most preferably an alkylene group having from 2 to 6 carbon atoms;

a group of formula

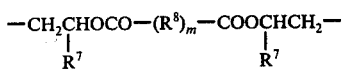

in which $R^7$ represents a hydrogen atom, a methyl group or a phenyl group, most preferably a hydrogen atom, m is 0 or 1 and $R^8$ represents an alkylene group having from 1 to 10 carbon atoms and which is optionally interrupted by a sulphur atom, e.g. a methylene, ethylene, tetramethylene, hexamethylene, octamethylene, decamethylene or 3-thiapentamethylene ($-CH_2CH_2SCH_2CH_2-$) group, an alkenylene group having 2 or 3 carbon atoms, e.g. a vinylene or 1,2-prop-2-enylene

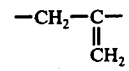

group, a phenylene group (o-phenylene, m-phenylene or p-phenylene) or a 1,4-cyclohexylene group, most preferably an alkylene group having from 2 to 8 carbon atoms.

Of the piperidine derivatives of general formula (I), a preferred class of compounds are those of formula (Ia)

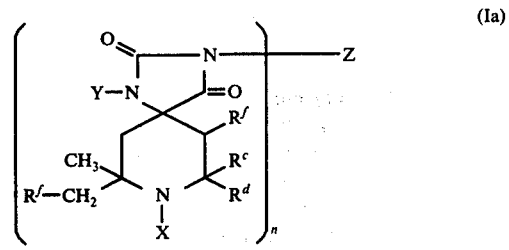

(in which $R^f$ represents a lower alkyl group, preferably having from 1 to 4 carbon atoms and $R^c$, $R^d$, X, Y, Z and n are as defined above). Within this preferred class, a more preferred class of compounds has the general formula (Ib):

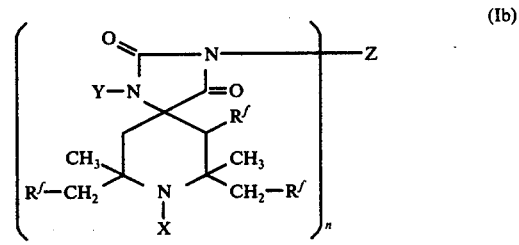

and the most preferred class of compounds are those of formula (Ic):

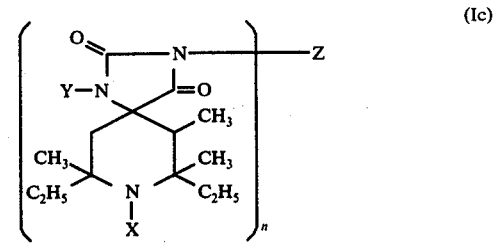

The most preferred compounds are those in which: X represents a hydrogen atom or a methyl group; Y represents a hydrogen atom; when $n = 1$, Z represents a hydrogen atom, an alkyl group having from 1 to 8 carbon atoms, an allyl group, a benzyl group, a 2,3-epoxypropyl group or a group of formula $-CH_2CH_2OCOR^{11}$ (in which $R^{11}$ represents: an alkyl group having from 1 to 17 carbon atoms; a phenyl group which is unsubstituted or has up to 3 $C_{1-4}$ alkyl and/or hydroxy substituents; or a 4-hydroxy-3,5-di-t-butylphenethyl group); or when $n = 2$, Z represents an alkylene group having from 2 to 6 carbon atoms or a p-xylylene group.

The invention also provides new acid addition salts of the piperidine derivatives of formula (I). The nature of the acid used to form such acid addition salts is not critical, provided that it does not adversely affect the stability of any polymer to be stabilized by the compound. Examples of suitable acids are: inorganic acids, such as sulphuric acid, hydrochloric acid or phosphoric acid; organic carboxylic acids, such as formic acid, acetic acid, valeric acid, stearic acid, oxalic acid, adipic acid, sebacic acid, maleic acid, benzoic acid, p-t-butylbenzoic acid, 4-hydroxy-3,5-di-t-butylbenzoic acid, salicylic acid or terephthalic acid; sulphonic acids, such as methanesulphonic acid or p-toluenesulphonic acid; or organic phosphonic acids, such as phenylphosphonic acid.

A single one of the piperidine derivatives (I) or an acid addition salt thereof may be employed as a stabilizer in a polymeric composition comprising one or more polymers; alternatively, a mixture of two or more such derivatives (I), two or more such acid addition salts or one or more such derivatives (I) with one or more such acid addition salts may be employed. In particular, since the piperidine derivatives (I), and hence their acid addition salts, can exist in the form of various stereoisomers, it is possible to employ a mixture of such stereoisomers or a mixture of the 6- and 10-positional isomers. Alternatively, at any stage during the synthesis of the derivatives (I) or their acid addition salts, the mixture of isomers which is usually obtained may be separated by conventional methods.

The following is a non-limiting list of individual piperidine derivatives of formula (I). The numbers appended to the compounds in this list will be used to identify them hereinafter in the Examples.

1. 7,9-diethyl-6,7,9-trimethyl-1,3,8-triazaspiro[4.5]decane-2,4-dione
2. 7,9-diethyl-3,6,7,9-tetramethyl-1,3,8-triazaspiro[4.5]decane-2,4-dione
3. 3,7,9-triethyl-6,7,9-trimethyl-1,3,8-triazaspiro[4.5]decane-2,4-dione
4. 3-butyl-7,9-diethyl-6,7,9-trimethyl-1,3,8-triazaspiro[4.5]decane-2,4-dione
5. 7,9-diethyl-6,7,9-trimethyl-3-octyl-1,3,8-triazaspiro[4.5]decane-2,4-dione
6. 7,9-diethyl-6,7,9-trimethyl-3-stearyl-1,3,8-triazaspiro[4.5]decane-2,4-dione
7. 3-allyl-7,9-diethyl-6,7,9-trimethyl-1,3,8-triazaspiro[4.5]decane-2,4-dione
8. 7,9-diethyl-6,7,9-trimethyl-3-(2-methyl-2-propenyl)-1,3,8-triazaspiro[4.5]decane-2,4-dione
9. 3-benzyl-7,9-diethyl-6,7,9-trimethyl-1,3,8-triazaspiro[4.5]decane-2,4-dione
10. 7,9-diethyl-6,7,9-trimethyl-3-(p-methylbenzyl)-1,3,8-triazaspiro[4.5]decane-2,4-dione
11. 3-(p-chlorobenzyl)-7,9-diethyl-6,7,9-trimethyl-1,3,8-triazaspiro[4.5]decane-2,4-dione
12. 7,9-diethyl-3-(4-hydroxy-3,5-di-t-butylbenzyl)-6,7,9-trimethyl-1,3,8-triazaspiro[4.5]decane-2,4-dione
13. 3-cyclohexyl-7,9-diethyl-6,7,9-trimethyl-1,3,8-triazaspiro[4.5]decane-2,4-dione
14. 7,9-diethyl-6,7,9-trimethyl-3-phenyl-1,3,8-triazaspiro[4.5]decane-2,4-dione
15. 7,9-diethyl-6,7,9-trimethyl-3-(p-tolyl)-1,3,8-triazaspiro[4.5]decane-2,4-dione
16. 3-(m-chlorophenyl)-7,9-diethyl-6,7,9-trimethyl-1,3,8-triazaspiro[4.5]decane-2,4-dione
17. 7,9-diethyl-6,7,9-trimethyl-3-(α-naphthyl)-1,3,8-triazaspiro[4.5]decane-2,4-dione
18. 3-(2,3-epoxypropyl)-7,9-diethyl-6,7,9-trimethyl-1,3,8-triazaspiro[4.5]decane-2,4-dione
19. 3-ethoxycarbonylmethyl-7,9-diethyl-6,7,9-trimethyl-1,3,8-triazaspiro[4.5]decane-2,4-dione
20. 7,9-diethyl-6,7,9-trimethyl-3-octoxycarbonyl-methyl-1,3,8-triazaspiro[4.5]decane-2,4-dione
21. 7,9-diethyl-6,7,9-trimethyl-3-phenoxycarbonylmethyl-1,3,8-triazaspiro[4.5]decane-2,4-dione
22. 7,9-diethyl-3-(2-hydroxyethyl)-6,7,9-trimethyl-1,3,8-triazaspiro[4.5]decane-2,4-dione
23. 7,9-diethyl-3-(2-hydroxypropyl)-6,7,9-trimethyl-1,3,8-triazaspiro[4.5]decane-2,4-dione
24. 7,9-diethyl-3-(2-hydroxy-2-phenylethyl)-6,7,9-trimethyl-1,3,8-triazaspiro[4.5]decane-2,4-dione
25. 3-(2-acetoxyethyl)-7,9-diethyl-6,7,9-trimethyl-1,3,8-triazaspiro[4.5]decane-2,4-dione
26. 7,9-diethyl-6,7,9-trimethyl-3-(2-octanoyloxyethyl)-1,3,8-triazaspiro[4.5]decane-2,4-dione
27. 7,9-diethyl-6,7,9-trimethyl-3-(2-stearoyloxyethyl)-1,3,8-triazaspiro[4.5]decane-2,4-dione
28. 3-(2-benzoyloxyethyl)-7,9-diethyl-6,7,9-trimethyl-1,3,8-triazaspiro[4.5]decane-2,4-dione
29. 7,9-diethyl-3-[2-(4-hydroxy-3,5-di-t-butylbenzoyloxy)ethyl]-6,7,9-trimethyl-1,3,8-triazaspiro[4.5]decane-2,4-dione
30. 7,9-diethyl-3-{2-[β-(4-hydroxy-3,5-di-t-butylphenyl)propionyloxy]ethyl}-6,7,9-trimethyl-1,3,8-triazaspiro[4.5]decane-2,4-dione
31. 3-(2-acetoxypropyl)-7,9-diethyl-6,7,9-trimethyl-1,3,8-triazaspiro[4.5]decane-2,4-dione
32. 7,9-diethyl-6,7,9-trimethyl-3-(2-stearoyloxypropyl)-1,3,8-triazaspiro[4.5]decane-2,4-dione
33. 3-(2-benzoyloxypropyl)-7,9-diethyl-6,7,9-trimethyl-1,3,8-triazaspiro[4.5]decane-2,4-dione
34. 3-(2-acetoxy-2-phenylethyl)-7,9-diethyl-6,7,9-trimethyl-1,3,8-triazaspiro[4.5]decane-2,4-dione
35. 7,9-diethyl-3-(2-methoxyethyl)-6,7,9-trimethyl-1,3,8-triazaspiro[4.5]decane-2,4-dione
36. 3-(2-ethoxyethyl)-7,9-diethyl-6,7,9-trimethyl-1,3,8-triazaspiro[4.5]decane-2,4-dione
37. 7,9-diethyl-6,7,9-trimethyl-3-(2-phenoxyethyl)-1,3,8-triazaspiro[4.5]decane-2,4-dione
38. 1,2-bis(7,9-diethyl-6,7,9-trimethyl-2,4-dioxo-1,3,8-triazaspiro[4.5]dec-3-yl)ethane
39. 1,4-bis(7,9-diethyl-6,7,9-trimethyl-2,4-dioxo-1,3,8-triazaspiro[4.5]dec-3-yl)butane
40. 1,6-bis(7,9-diethyl-6,7,9-trimethyl-2,4-dioxo-1,3,8-triazaspiro[4.5]dec-3-yl)hexane
41. di[2-(7,9-diethyl-6,7,9-trimethyl-2,4-dioxo-1,3,8-triazaspiro[4.5]dec-3-yl)ethyl]ether
42. trans-1,4-bis(7,9-diethyl-6,7,9-trimethyl-2,4-dioxo-1,3,8-triazaspiro[4.5]dec-3-yl)but-2-ene
43. p-bis(7,9-diethyl-6,7,9-trimethyl-2,4-dioxo-1,3,8-triazaspiro[4.5]dec-3-ylmethyl)benzene
44. m-bis(7,9-diethyl-6,7,9-trimethyl-2,4-dioxo-1,3,8-triazaspiro[4.5]dec-3-ylmethyl)benzene
45. p-bis(7,9-diethyl-6,7,9-trimethyl-2,4-dioxo-1,3,8-triasprio[4.5]dec-3-yl)benzene
46. 1,3-bis(7,9-diethyl-6,7,9-trimethyl-2,4-dioxo-1,3,8-triazaspiro[4.5]dec-3-yl)-4-methylbenzene
47. 1,5-bis(7,9-diethyl-6,7,9-trimethyl-2,4-dioxo-1,3,8-triazaspiro[4.5]dec-3-yl)naphthalene
48. di[p-(7,9-diethyl-6,7,9-trimethyl-2,4-dioxo-1,3,8-triazaspiro[4.5]dec-3-yl)phenyl]ether
49. bis[p-(7,9-diethyl-6,7,9-trimethyl-2,4-dioxo-1,3,8-triazaspiro[4.5]dec-3-yl)phenyl]methane
50. 1,2-bis(7,9-diethyl-6,7,9-trimethyl-2,4-dioxo-1,3,8-triazaspiro[4.5]dec-3-ylacetoxy)ethane 51. 1,4-bis(7,9-diethyl-6,7,9-trimethyl-2,4-dioxo-1,3,8-triazaspiro[4.5]dec-3-ylacetoxy)butane
52. 1,6-bis(7,9-diethyl-6,7,9-trimethyl-2,4-dioxo-1,3,8-triazaspiro[4.5]dec-3-ylacetoxy)hexane
53. bis[2-(7,9-diethyl-6,7,9-trimethyl-2,4-dioxo-1,3,8-triazaspiro[4.5]dec-3-yl)ethyl]succinate
54. bis[2-(7,9-diethyl-6,7,9-trimethyl-2,4-dioxo-1,3,8-triazaspiro[4.5]dec-3-yl)ethyl]adipate
55. bis[2-(7,9-diethyl-6,7,9-trimethyl-2,4-dioxo-1,3,8-triazaspiro[4.5]dec-3-yl)ethyl]sebacate
56. bis[2-(7,9-diethyl-6,7,9-trimethyl-2,4-dioxo-1,3,8-triazaspiro[4.5]dec-3-yl)ethyl]terephthalate
57. bis[2-(7,9-diethyl-6,7,9-trimethyl-2,4-dioxo-1,3,8-triazaspiro[4.5]dec-3-yl)ethyl]isophthalate
58. bis[2-(7,9-diethyl-6,7,9-trimethyl-2,4-dioxo-1,3,8-triazaspiro[4.5]dec-3-yl)-1-methylethyl]succinate
59. 7,9-diethyl-6,7,9-trimethyl-1,3,8-triazaspiro[4.5]decane-2,4-dione-8-oxyl
60. 7,9-diethyl-3,6,7,9-tetramethyl-1,3,8-triazaspiro[4.5]decane-2,4-dione-8-oxyl
61. 3-benzyl-7,9-diethyl-6,7,9-trimethyl-1,3,8-triazaspiro[4.5]decane-2,4-dione-8-oxyl
62. 1,4-bis(7,9-diethyl-6,7,9-trimethyl-2,4-dioxo-8-oxyl-1,3,8-triazaspiro[4.5]dec-3-yl)butane
63. 7,9-diethyl-6,7,8,9-tetramethyl-1,3,8-triazaspiro[4.5]decane-2,4-dione
64. 7,9-diethyl-3,6,7,8,9-pentamethyl-1,3,8-triazaspiro[4.5]decane-2,4-dione
65. 3-butyl-7,9-diethyl-6,7,8,9-tetramethyl-1,3,8-triazaspiro[4.5]decane-2,4-dione
66. 7,9-diethyl-6,7,8,9-tetramethyl-3-octyl-1,3,8-triazaspiro[4.5]decane-2,4-dione
67. 3-(2,3-epoxypropyl)-7,9-diethyl-6,7,8,9-tetramethyl-1,3,8-triazaspiro[4.5]decane-2,4-dione
68. 3-allyl-7,9-diethyl-6,7,8,9-tetramethyl-1,3,8-triazaspiro[4.5]decane-2,4-dione
69. 3-benzyl-7,9-diethyl-6,7,8,9-tetramethyl-1,3,8-triazaspiro[4.5]decane-2,4-dione
70. 7,9-diethyl-6,7,8,9-tetramethyl-3-phenyl-1,3,8-triazaspiro[4.5]decane-2,4-dione
71. 3-ethoxycarbonylmethyl-7,9-diethyl-6,7,8,9-tetramethyl-1,3,8-triazaspiro[4.5]decane-2,4-dione
72. 3-(2-acetoxyethyl)-7,9-diethyl-6,7,8,9-tetramethyl-1,3,8-triazaspiro[4.5]decane-2,4-dione
73. 3-(2-benzoyloxyethyl)-7,9-diethyl-6,7,8,9-tetramethyl-1,3,8-triazaspiro[4.5]decane-2,4-dione
74. 3-(2-ethoxyethyl)-7,9-diethyl-6,7,8,9-tetramethyl-1,3,8-triazaspiro[4.5]decane-2,4-dione
75. 1,2-bis(7,9-diethyl-6,7,8,9-tetramethyl-2,4-dioxo-1,3,8-triazaspiro[4.5]dec-3-yl)ethane
76. 1,4-bis(7,9-diethyl-6,7,8,9-tetramethyl-2,4-dioxo-1,3,8-triazaspiro[4.5]dec-3-yl)butane
77. 1,6-bis(7,9-diethyl-6,7,8,9-tetramethyl-2,4-dioxo-1,3,8-triazaspiro[4.5]dec-3-yl)hexane
78. p-bis(7,9-diethyl-6,7,8,9-tetramethyl-2,4-dioxo-1,3,8-triazaspiro[4.5]dec-3-ylmethyl)benzene
79. m-bis(7,9-diethyl-6,7,8,9-tetramethyl-2,4-dioxo-1,3,8-triazaspiro[4.5]dec-3-ylmethyl)benzene
80. 1,2-bis(7,9-diethyl-6,7,8,9-tetramethyl-2,4-dioxo-1,3,8-triazaspiro[4.5]dec-3-ylacetoxy)ethane
81. 1,4-bis(7,9-diethyl-6,7,8,9-tetramethyl-2,4-dioxo-1,3,8-triazaspiro[4.5]dec-3-ylacetoxy)butane
82. bis[2-(7,9-diethyl-6,7,8,9-tetramethyl-2,4-dioxo-1,3,8-triazaspiro[4.5]dec-3-yl)ethyl]adipate
83. bis[2-(7,9-diethyl-6,7,8,9-tetramethyl-2,4-dioxo-1,3,8-triazaspiro[4.5]dec-3-yl)ethyl]sebacate
84. bis[2-(7,9-diethyl-6,7,8,9-tetramethyl-2,4-dioxo-1,3,8-triazaspiro[4.5]dec-3-yl)ethyl]terephthalate
85. bis[2-(7,9-diethyl-6,7,8,9-tetramethyl-2,4-dioxo-1,3,8-triazaspiro[4.5]dec-3-yl]isophthalate
86. 8-allyl-7,8-diethyl-6,7,9-trimethyl-1,3,8-triazaspiro[4.5]decane-2,4-dione
87. 8-allyl-7,9-diethyl-3,6,7,9-tetramethyl-1,3,8-triazaspiro[4.5]decane-2,4-dione
88. 8-allyl-3-butyl-7,9-diethyl-6,7,9-trimethyl-1,3,8-triazaspiro[4.5]decane-2,4-dione
89. 3,8-diallyl-7,9-diethyl-6,7,9-trimethyl-1,3,8-triazaspiro[4.5]decane-2,4-dione
90. 8-allyl-3-benzyl-7,9-diethyl-6,7,9-trimethyl-1,3,8-triazaspiro[4.5]decane-2,4-dione
91. 3-(2-acetoxyethyl)-8-allyl-7,9-diethyl-6,7,9-trimethyl-1,3,8-triazaspiro[4.5]decane-2,4-dione
92. 1,2-bis(8-allyl-7,9-diethyl-6,7,9-trimethyl-2,4-dioxo-1,3,8-triazaspiro[4.5]dec-3-yl)ethane
93. 1,4-bis(8-allyl-7,9-diethyl-6,7,9-trimethyl-2,4-dioxo-1,3,8-triazaspiro[4.5]dec-3-yl)butane
94. p-bis(8-allyl-7,9-diethyl-6,7,9-trimethyl-2,4-dioxo-1,3,8-triazaspiro[4.5]dec-3-ylmethyl)benzene
95. 1,2-bis(8-allyl-7,9-diethyl-6,7,9-trimethyl-2,4-dioxo-1,3,8-triazaspiro[4.5]dec-3-ylacetoxy)ethane
96. di[p-(8-allyl-7,9-diethyl-6,7,9-trimethyl-2,4-dioxo-1,3,8-triazaspiro[4.5]dec-3-yl)phenyl]ether
97. bis[2-(8-allyl-7,9-diethyl6,7,9-trimethyl-2,4-dioxo-1,3,8-triazaspiro[4.5]dec-3-yl)ethyl]sebacate
98. 8-benzyl-7,9-diethyl-6,7,9-trimethyl-1,3,8-triazaspiro[4.5]decane-2,4-dione
99. 8-benzyl-7,9-diethyl-3,6,7,9-tetramethyl-1,3,8-triazaspiro[4.5]decane-2,4-dione
100. 8-benzyl-7,9-diethyl-6,7,9-trimethyl-3-octyl-1,3,8-triazaspiro[4.5]decane-2,4-dione
101. 3,8-dibenzyl-7,9-diethyl-6,7,9-trimethyl-1,3,8-triazaspiro[4.5]decane-2,4-dione
102. 8-benzyl-3-ethoxycarbonylmethyl-7,9-diethyl-6,7,9-trimethyl-1,3,8-triazaspiro[4.5]decane-2,4-dione
103. 3-(2-acetoxyethyl)-8-benzyl-7,9-diethyl-6,7,9-trimethyl-1,3,8-triazaspiro[4.5]decane-2,4-dione
104. 3-(2-benzoyloxyethyl)-8-benzyl-7,9-diethyl-6,7,9-trimethyl-1,3,8-triazaspiro[4.5]decane-2,4-dione
105. 1,2-bis(8-benzyl-7,9-diethyl-6,7,9-trimethyl-2,4-dioxo-1,3,8-triazaspiro[4.5]dec-3-yl)ethane
106. 1,6-bis(8-benzyl-7,9-diethyl-6,7,9-trimethyl-2,4-dioxo-1,3,8-triazaspiro[4.5]dec-3-yl)hexane
107. p-bis(8-benzyl-7,9-diethyl-6,7,9-trimethyl-2,4-dioxo-1,3,8-triazaspiro[4.5]dec-3-ylmethyl)benzene
108. bis[p-(8-benzyl-7,9-diethyl-6,7,9-trimethyl-2,4-dioxo-1,3,8-triazaspiro[4.5]dec-3-yl)phenyl]methane
109. 1,3-bis(8-benzyl-7,9-diethyl-6,7,9-trimethyl-2,4-dioxo-1,3,8-triazaspiro[4.5]dec-3-yl)-4-methylbenzene
110. 1,2-bis(8-benzyl-7,9-diethyl-6,7,9-trimethyl-2,4-dioxo-1,3,8-triazaspiro[4.5]dec-3-ylacetoxy)ethane
111. bis[2-(8-benzyl-7,9-diethyl-6,7,9-trimethyl-2,4-dioxo-1,3,8-triazaspiro[4.5]dec-3-yl)ethyl]adipate
112. bis[2-(8-benzyl-7,9-diethyl-6,7,9-trimethyl-2,4-dioxo-1,3,8-triazaspiro[4.5]dec-3-yl)ethyl]terephthalate
113. 8-(2,3-epoxypropyl)-7,9-diethyl-6,7,9-trimethyl-1,3,8-triazaspiro[4.5]decane-2,4-dione
114. 8-(2,3-epoxypropyl)-7,9-diethyl-3,6,7,9-tetramethyl-1,3,8-triazaspiro[4.5]decane-2,4-dione
115. 3,8-di(2,3-epoxypropyl)-7,9-diethyl-6,7,9-trimethyl-1,3,8-triazaspiro[4.5]decane-2,4-dione
116. 3-allyl-8-(2,3-epoxypropyl)-7,9-diethyl-6,7,9-trimethyl-1,3,8-triazaspiro[4.5]decane-2,5-dione
117. 1,4-bis[8-(2,3-epoxypropyl)-7,9-diethyl-6,7,9-trimethyl-1,3,8-triazaspiro[4.5]dec-3-yl]butane 118. 7,9-diethyl-8-(2-hydroxyethyl)-6,7,9-trimethyl-3-octyl-1,3,8-triazaspiro[4.5]decane-2,4-dione
119. p-bis[7,9-diethyl-8-(2-hydroxyethyl)-6,7,9-trimethyl-2,4-dioxo-1,3,8-triazaspiro[4.5]dec-3-ylmethyl]benzene
120. 8-(2-acetoxyethyl)-7,9-diethyl-6,7,9-trimethyl-1,3,8-triazaspiro[4.5]decane-2,4-dione
121. 8-(2-acetoxyethyl)-7,9-diethyl-3,6,7,9-tetramethyl-1,3,8-triazaspiro[4.5]decane-2,4-dione
122. 8-(2-acetoxyethyl)-7,9-diethyl-6,7,9-trimethyl-3-octyl-1,3,8-triazaspiro[4.5]decane-2,4-dione
123. 8-(2-acetoxyethyl)-3-benzyl-7,9-diethyl-6,7,9-trimethyl-1,3,8-triazaspiro[4.5]decane-2,4-dione
124. 1,2-bis[8-(2-acetoxyethyl)-7,9-diethyl-6,7,9-trimethyl-2,4-dioxo-1,3,8-triazaspiro[4.5]dec-3-yl]ethane
125. p-bis[8-(2-acetoxyethyl)-7,9-diethyl-6,7,9-trimethyl-2,4-dioxo-1,3,8-triazaspiro[4.5]dec-3-ylmethyl]benzene
126. bis{2-[8-(2-acetoxyethyl)-7,9-diethyl-6,7,9-trimethyl-2,4-dioxo-1,3,8-triazaspiro[4.5]dec-3-yl]ethyl}•isophthalate
127. 3,8-di(2-acetoxyethyl)-7,9-diethyl-6,7,9-trimethyl-1,3,8-triazaspiro[4.5]decane-2,4-dione
128. 8-(2-benzoyloxyethyl)-7,9-diethyl-6,7,9-trimethyl-1,3,8-triazaspiro[4.5]decane-2,4-dione
129. 8-(2-benzoyloxyethyl)-7,9-diethyl-3,6,7,9-tetramethyl-1,3,8-triazaspiro[4.5]decane-2,4-dione
130. 8-(2-benzoyloxyethyl)-7,9-diethyl-6,7,9-trimethyl-3-octyl-1,3,8-triazaspiro[4.5]decane-2,4-dione
131. 8-(2-benzoyloxyethyl)-3-benzyl-7,9-diethyl-6,7,9-trimethyl-1,3,8-triazaspiro[4.5]decane-2,4-dione
132. 3,8-di(2-benzoyloxyethyl)-7,9-diethyl-6,7,9-trimethyl-1,3,8-triazaspiro[4.5]decane-2,4-dione
133. 1,4-bis[8-(2-benzoyloxyethyl)-7,9-diethyl-6,7,9-trimethyl-2,4-dioxo-1,3,8-triazaspiro[4.5]dec-3-yl]butane
134. 1,2-bis[8-(2-benzoyloxyethyl)-7,9-diethyl-6,7,9-trimethyl-2,4-dioxo-1,3,8-triazaspiro[4.5]dec-3-ylacetoxy]ethane
135. bis{2-[8-(2-benzoyloxyethyl)-7,9-diethyl-6,7,9-trimethyl-2,4-dioxo-1,3,8-triazaspiro[4.5]dec-3-yl]ethyl}adipate
136. 7,9-diethyl-1,3,6,7,8,9-hexamethyl-1,3,8-triazaspiro[4.5]decane-2,4-dione
137. 3-butyl-7,9-diethyl-1,6,7,8,9-pentamethyl-1,3,8-triazaspiro[4.5]decane-2,4-dione
138. 3-benzyl-7,9-diethyl-1,6,7,8,9-pentamethyl-1,3,8-triazaspiro[4.5]decane-2,4-dione
139. 3-allyl-7,9-diethyl-1,6,7,8,9-pentamethyl-1,3,8-triazaspiro[4.5]decane-2,4-dione
140. p-bis(7,9-diethyl-1,6,7,8,9-pentamethyl-2,4-dioxo-1,3,8-triazaspiro[4.5]dec-3-ylmethyl)benzene
141. 1,4-bis(7,9-diethyl-1,6,7,8,9-pentamethyl-2,4-dioxo-1,3,8-triazaspiro[4.5]dec-3-yl)butane
142. 1-benzyl-7,9-diethyl-6,7,8,9-tetramethyl-3-octyl-1,3,8-triazaspiro[4.5]decane-2,4-dione
143. 1,3-dibenzyl-7,9-diethyl-6,7,8,9-tetramethyl-1,3,8-triazaspiro[4.5]decane-2,4-dione
144. 3-(2-acetoxyethyl)-1-benzyl-7,9-diethyl-6,7,8,9-tetramethyl-1,3,8-triazaspiro[4.5]decane-2,4-dione
145. 1,2-bis(1-benzyl-7,9-diethyl-6,7,8,9-tetramethyl-2,4-dioxo-1,3,8-triazaspiro[4.5]dec-3-yl)ethane
146. 6-ethyl-7,9-dimethyl-7,9-dipropyl-1,3,8-triazaspiro[4.5]decane-2,4-dione
147. 3-benzyl-6-ethyl-7,9-dimethyl-7,9-dipropyl-1,3,8-triazaspiro[4.5]decane-2,4-dione
148. 6-isobutyl-7,9-diisopentyl-7,9-dimethyl-1,3,8-triazaspiro[4.5]decane-2,4-dione
149. 3-benzyl-6-isobutyl-7,9-diisopentyl-7,9-dimethyl-1,3,8-triazaspiro[4.5]decane-2,4-dione
150. 7,7-dibutyl-9-ethyl-6,9-dimethyl-1,3,8-triazaspiro[4.5]decane-2,4-dione
151. 9-ethyl-6,7,9-trimethyl-7-phenyl-1,3,8-triazaspiro[4.5]decane-2,4-dione
152. 9-ethyl-6,7,9-trimethyl-3-octyl-7-phenyl-1,3,8-triazaspiro[4.5]decane-2,4-dione
153. 9-ethyl-6,7,9-trimethyl-7-phenethyl-1,3,8-triazaspiro[4.5]decane-2,4-dione
154. 14-ethyl-6,14-dimethyl-1,3,13-triazadispiro[4.1.5.3]pentadecane-2,4-dione
155. 3-butyl-14-ethyl-6,14-dimethyl-1,3,13-triazadispiro[4.1.5.3]pentadecane-2,4-dione
156. 13-ethyl-6,13-dimethyl-1,3,12-triazadispiro[4.1.4.3]tetradecane-2,4-dione
157. 7,7,9,9-tetramethyl-6-propyl-1,3,8-triazaspiro[4.5]decane-2,4-dione
158. 3-benzyl-7,7,9,9-tetramethyl-6-propyl-1,3,8-triazaspiro[4.5]decane-2,4-dione
159. 6-allyl-7,7,9,9-tetramethyl-1,3,8-triazaspiro[4.5]decane-2,4-dione The piperidine derivatives (I) of the present invention may be prepared by the following methods, which can be performed under known conditions:

METHOD 1

Compounds of formula (I-1) may be prepared by reacting a 4-piperidone derivative of formula (II) with ammonium hydrogen carbonate or ammonium carbonate and potassium cyanide by the method described in J. Org. Chem. 22, 1061 (1957):

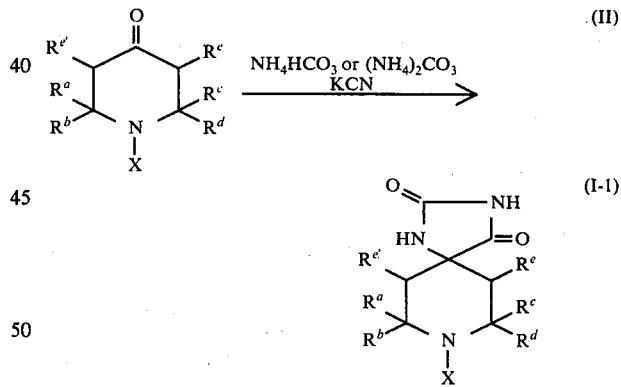

(in which $R^a$, $R^b$, $R^c$, $R^d$, $R^e$, $R^{e'}$ and X are as defined above).

METHOD 2

Compounds of formula (I-2) may be prepared by reacting a 4-piperidone derivative of formula (II) with hydrogen cyanide and ammonium to form a 4-amino-4-cyanopiperidine derivative of formula (III) by a known method, reacting the 4-amino-4-cyanopiperidine derivative (III) with an isocyanate to form a 4-cyano-4-ureidopiperidine derivative of formula (IV) and finally treating the 4-cyano-4-ureidopiperidine derivative (IV) with an aqueous solution of a mineral acid, in accordance with the method described in U.S. Pat. No. 3,639,409:

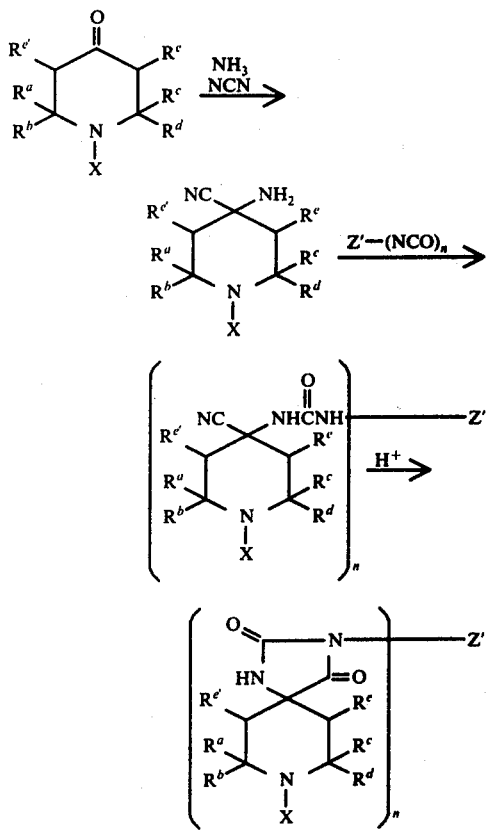

(II)

(III)

(IV)

(I-2)

wherein: $R^a$, $R^b$, $R^c$, $R^d$, $R^e$, $R^{e'}$, $n$ and X are as defined above; and Z' represents, when $n = 1$, an alkyl group, an aryl group (which is unsubstituted or has one or more chlorine or methyl substituents) or a cyclohexyl group, and, when $n = 2$, an alkylene group, an arylene group (which is unsubstituted or has one or more methyl substituents) or the group

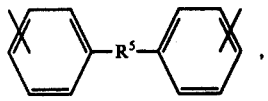

$R^5$ being as defined above.

METHOD 3

Compounds of formula (I-3) may be prepared by reacting an alkali metal salt of compound (I-1) with a halide by the method described in German Offenlegungsschrift No. 2,233,121:

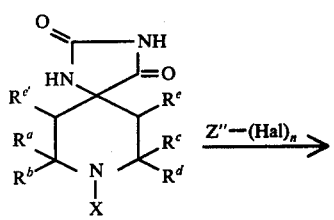

(I-1)

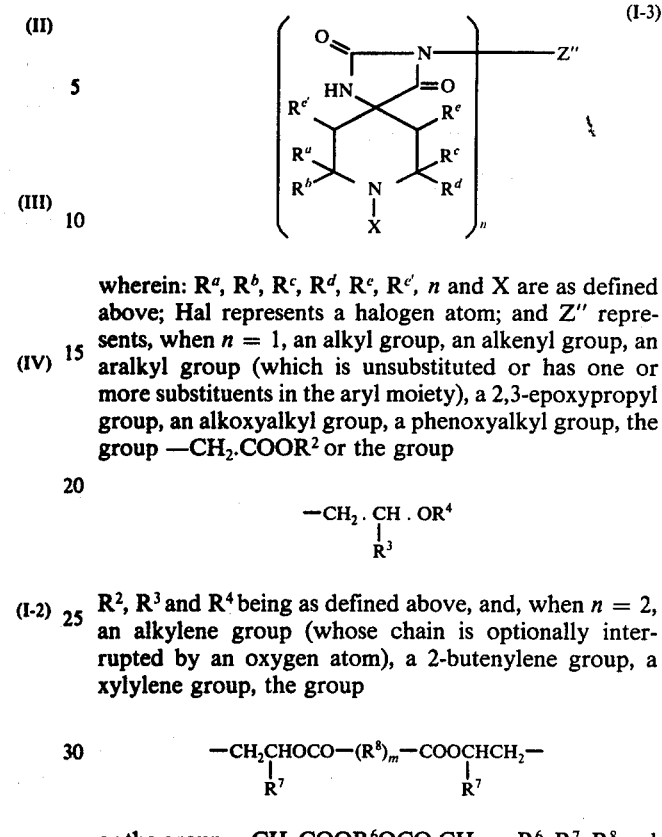

(I-3)

wherein: $R^a$, $R^b$, $R^c$, $R^d$, $R^e$, $R^{e'}$, $n$ and X are as defined above; Hal represents a halogen atom; and Z" represents, when $n = 1$, an alkyl group, an alkenyl group, an aralkyl group (which is unsubstituted or has one or more substituents in the aryl moiety), a 2,3-epoxypropyl group, an alkoxyalkyl group, a phenoxyalkyl group, the group —$CH_2 \cdot COOR^2$ or the group

$R^2$, $R^3$ and $R^4$ being as defined above, and, when $n = 2$, an alkylene group (whose chain is optionally interrupted by an oxygen atom), a 2-butenylene group, a xylylene group, the group

or the group —$CH_2COOR^6OCO.CH_2$—, $R^6$, $R^7$, $R^8$ and $m$ being as defined above.

METHOD 4

Compounds of formula (I-4) may be prepared by reacting a compound of formula (I-5) with a peroxide, such as hydrogen peroxide, by the method described in U.S. Pat. No. 3,536,722 or Japanese Pat. Publication No. 46-39105:

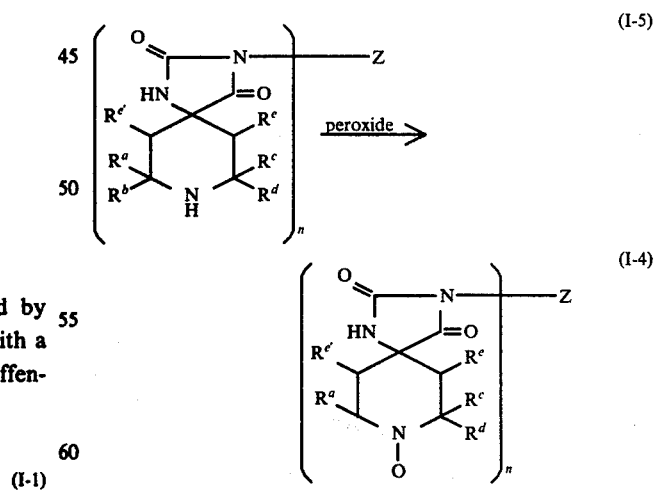

wherein $R^a$, $R^b$, $R^c$, $R^d$, $R^e$, $R^{e'}$, $n$ and Z are as defined above.

METHOD 5

Compounds of formula (I-6) may be prepared by reacting a compound of formula (I-5) with formaldehyde and formic acid by means of the Leuckart-Wallach reaction:

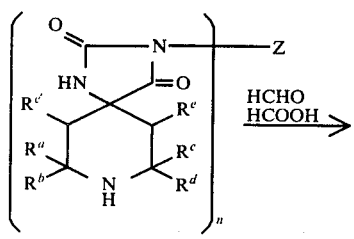

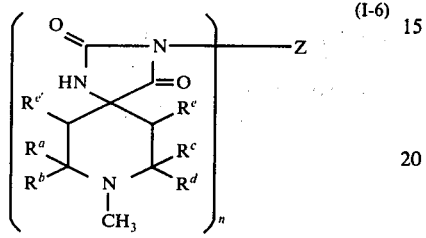

wherein $R^a$, $R^b$, $R^c$, $R^d$, $R^e$, $R^{e'}$, n and Z are as defined above.

METHOD 6

Compounds of formula (I-7) may be prepared by reacting a compound of formula (I-8) with a halide:

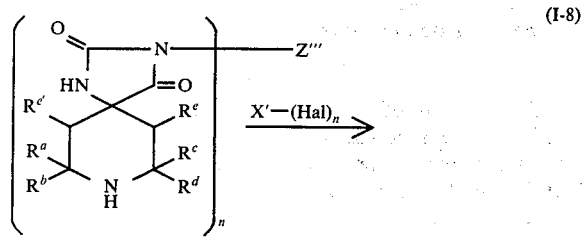

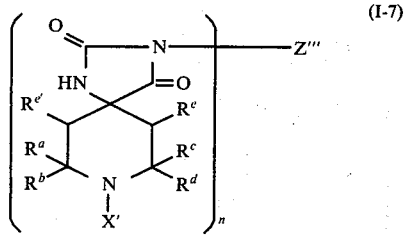

wherein: $R^a$, $R^b$, $R^c$, $R^d$, $R^e$, $R^{e'}$, n and Hal are as defined above; X' represents an alkenyl group or a benzyl group; and Z''' has the same meanings as Z except for a hydrogen atom.

METHOD 7

Compounds of formula (I-9) may be prepared by reacting a compound of formula (I-8) with ethylene oxide in the presence of an acid catalyst, such as sulphuric acid or hydrochloric acid. The 2-hydroxyethyl compound thus obtained may then be acylated to form the corresponding 2-acyloxyethyl compound of formula (I-10):

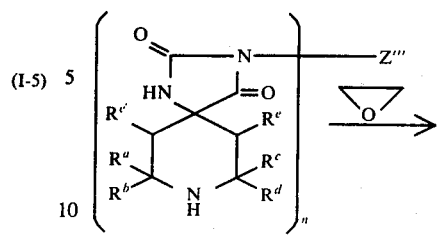

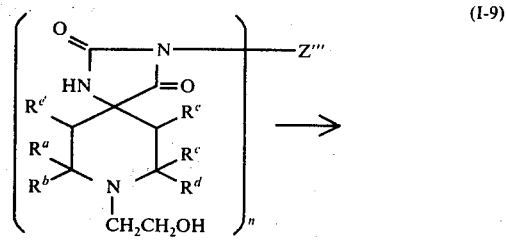

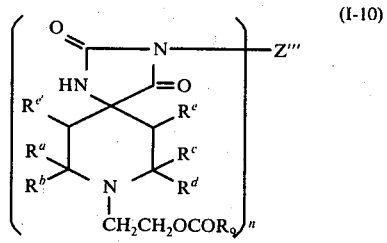

wherein $R^a$, $R^b$, $R^c$, $R^d$, $R^e$, $R^{e'}$, n, $R^9$ and Z''' are as defined above.

METHOD 8

Compounds of formula (I-11) may be prepared by reacting a compound of formula (I-12) or an alkali metal salt thereof with a halide:

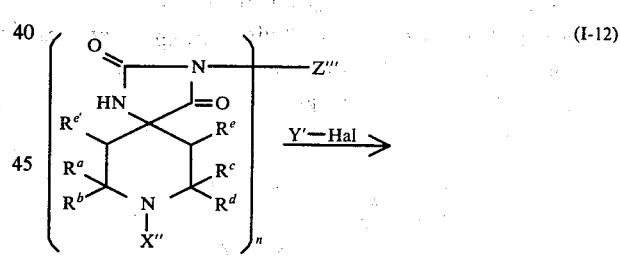

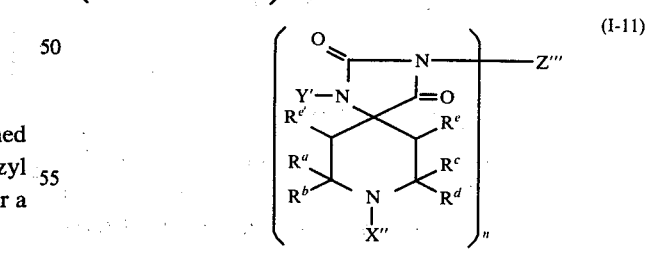

wherein: $R^a$, $R^b$, $R^c$, $R^d$, $R^e$, $R^{e'}$, n, Hal and Z''' are as defined above; Y' has the same meanings as Y, except for a hydrogen atom; and X'' has the same meanings as X, except for a hydrogen atom.

METHOD 9

Compounds of formula (I-13) may be prepared by reacting a compound of formula (I-14) with a dialkyl sulphate:

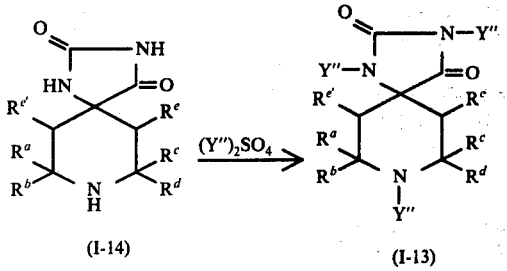

(I-14)     (I-13)

wherein: $R^a$, $R^b$, $R^c$, $R^d$, $R^e$ and $R^{e'}$ are as defined above and Y″ represents an alkyl group, preferably a methyl or ethyl group.

One of the starting materials for preparing the piperidine derivatives of the invention is the 4-piperidone derivative (II); this may be prepared by any of the following Methods A to F, which may be summarized in the following reaction scheme:

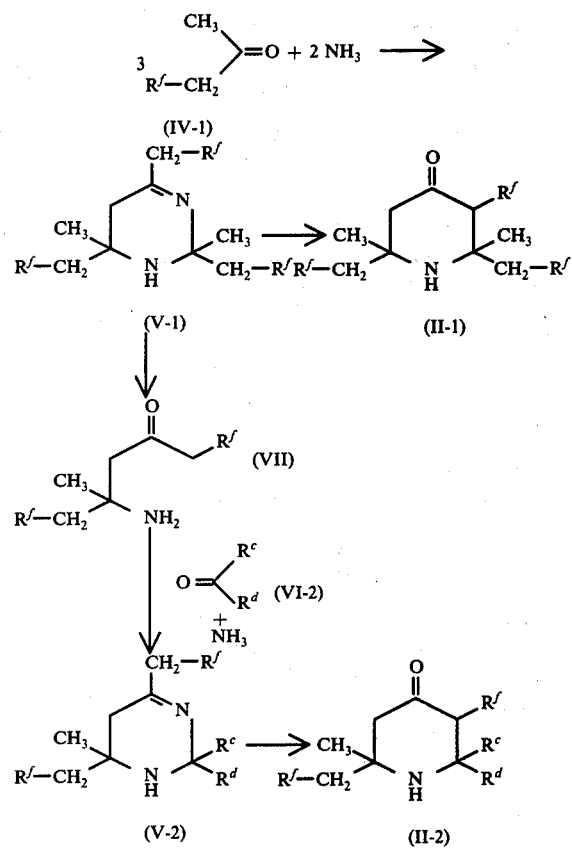

In the above formulae, $R^f$, $R^c$ and $R^d$ are as defined above.

METHOD A

According to the method described in Berichte 41, 777 (1908), a ketone of formula (VI-1) is brought into contact for a long time with ammonia in the presence of an alcohol to produce directly the desired 4-piperidone derivative of formula (II-1).

METHOD B

A ketone of formula (VI-1) is reacted with ammonia in the presence of an acid catalyst to give a 1,2,5,6-tetrahydropyrimidine derivative of formula (V-1), by the method described in U.S. Pat. No. 2,516,626. This tetrahydropyrimidine derivative is then treated with an organic sulphonic acid (e.g. p-toluenesulphonic acid or benzenesulphonic acid), a mineral acid (e.g. hydrochloric acid or sulphuric acid), or an ammonium salt of a mineral acid (e.g. ammonium chloride or ammonium bromide) or a mixture of these, in the presence of a small amount of water, to give a 4-piperidone derivative of formula (II-1) having the same substituent at the 2- and 6-positions.

METHOD C

According to the method described in U.S. Pat. No. 3,513,170, a 4-piperidone derivative of formula (II-1) is prepared by reacting a tetrahydropyrimidine derivative of formula (V-1) with water in the presence of a Lewis acid, such as calcium chloride or zinc chloride.

METHOD D

The tetrahydropyrimidine derivative of formula (V-1) may, as an alternative, be converted to an aminoketone derivative of formula (VII) by treating it with an aqueous solution of a strong acid (e.g. hydrochloric acid or sulphuric acid) by the method described in Helv. Chim. Acta 30, 1114 (1947). The aminoketone derivative (VII) thus obtained is reacted with a ketone of formula (VI-2) and ammonia to give a 1,2,5,6-tetrahydropyrimidine derivative of formula (V-2) having different substituents at the 2- and the 6-positions, employing the method described in Monatsh. Chem. 88, 464 (1957). This tetrahydropyrimidine derivative is then treated by any of the procedures described above in relation to tetrahydropyrimidine derivative (V-1) to give the corresponding 4-piperidone derivative of formula (II-2), having different substituents at the 2- and 6-positions.

METHOD E

A 2,2,6,6-tetrasubstituted 4-piperidone derivative which is unsubstituted at the 3- or 5-position is reacted with a secondary amine, such as piperidine or morpholine to give a corresponding enamine which is then reacted with a halogenated hydrocarbon (such as allyl bromide) by the method of, for example, J. Szmuszkovicz, Adv. Org. Chem. 4, 2 (1963); the reaction product thus obtained is hydrolized, giving a compound having a hydrocarbon radical at the 3- or 5-position. If desired, if the hydrocarbon radical introduced at the 3- or 5-position is unsaturated, it may be reduced by conventional methods to give a corresponding saturated hydrocarbon radical.

METHOD F 4-piperidone derivatives of formula (II) in which X is other than a hydrogen atom may be prepared by applying substantially the same procedures as are described in Methods 4, 5, 6 or 7 to the corresponding 4-piperidone derivative wherein X represents a hydrogen atom.

The piperidine derivatives (I) of the present invention will effectively stabilize polymers, particularly synthetic polymers, against the deterioration caused by heat and/or light. Accordingly, the present invention further consists in a polymeric composition comprising a polymer and, as stabilizer, a piperidine derivative of formula (I). Organic polymers which can be stabilized in this way include:
olefin and diene polymers including homopolymers of olefins and dienes (e.g. low-density, high-density and cross-linked polyethylenes, polypropylene, polyisobutylene, polymethylbutene-1, polymethylpentene-1, polyisoprene and polybutadiene), mixtures of such homopolymers (e.g. mixtures of polypropylene and polyethylene, polypropylene and polybutene-1, or polypropylene and polyisobutylene), and copolymers of olefins and dienes (e.g. ethylene/propylene copolymers, propylene/butene-1 copolymers, propylene/isobutylene copolymers, ethylene/butene-1 copolymers, and terpolymers of ethylene and propylene with dienes such as hexadiene, dicyclopentadiene or ethylidene norbornene);

styrene polymers
including polystyrene, copolymers of styrene and of α-methylstyrene (e.g. styrene/butadiene copolymers, styrene/acrylonitrile copolymers, styrene/acrylonitrile/methylmethacrylate copolymers, styrene/acrylonitrile/acrylic ester copolymers, styrene/acrylonitrile copolymers modified with acrylic ester polymers to provide impact strength, and styrene polymers modified with ethylene/propylene/diene elastomers to provide impact strength), and graft copolymers of styrene (e.g. polymers in which styrene is grafted onto polybutadiene, and polymers in which styrene and acrylonitrile are grafted onto polybutadiene as well as mixtures thereof with the aforementioned styrene copolymers commonly known as acrylonitrile/butadiene/styrene or ABS plastics);

halogenated vinyl and vinylidene polymers
including polyvinyl chloride, polyvinylidene chloride, polyvinyl fluoride, polychloroprene, chlorinated rubbers, vinyl chloride/vinylidene chloride copolymers, vinyl chloride/vinyl acetate copolymers, and vinylidene chloride/vinyl acetate copolymers;

polymers derived from α,β-unsaturated acids
and derivatives thereof, including polyacrylates and polymethacrylates, polyacrylic amides and polyacrylonitrile;

polymers derived from unsaturated alcohols and amines
and from the acyl derivatives thereof or acetals, including polyvinyl alcohol, polyvinyl acetate, polyvinyl stearate, polyvinyl benzoate, polyvinyl maleate, polyvinyl butyral, polyallyl phthalate, and polyallyl melamine, and copolymers thereof with other ethylenically unsaturated monomers (e.g. ethylene/vinyl acetate copolymers);

epoxy polymers
including homopolymers and copolymers derived from epoxides (e.g. polyethylene oxide), and polymers derived from bis-glycidyl ethers;

polyacetals, polyalkylene oxides and polyphenylene oxides
including polyoxymethylene, oxymethylene/ethylene oxide copolymers, polyoxyethylene, polypropylene oxide, polyisobutylene oxide and polyphenylene oxides;

polyurethanes and polyureas;
polycarbonates;
polysulphones;
polyamides and copolyamides
derived from diamines and dicarboxylic acids and/or from amino-carboxylic acids or the corresponding lactams, including nylon-6, nylon-6,6, nylon-6,10, nylon-11 and nylon-12;

polyesters
derived from dicarboxylic acids and dialcohols and/or from hydroxycarboxylic acids and the corresponding lactones, e.g. polyethylene glycol terephthalate and poly-1,4-dimethylol-cyclohexane terephthalate;

cross-linked polymers
derived from aldehydes together with phenols, ureas or melamines, e.g. phenol/formaldehyde, urea/formaldehyde and melamine/formaldehyde resins;

alkyd resins
e.g. glycerol/phthalic acid resins and mixtures thereof with melamine/formaldehyde resins;

unsaturated polyester resins
derived from copolyesters of saturated and unsaturated dicarboxylic acids with polyhydric alcohols as well as from vinyl compounds as cross-linking agents, and also halogenated flame-resistant modifications thereof; and natural polymers
including cellulose, rubber and proteins, as well as chemically modified homologues thereof (e.g. cellulose acetates, cellulose propionates, cellulose butyrates and cellulose ethers such as methyl cellulose).

The amount of the stabilizers of the invention needed for effective stabilization of organic polymers will depend on a variety of factors, such as the type and properties of the polymer concerned, its intended use, and the presence of other stabilizers. It is generally satisfactory to use from 0.01% to 5% by weight of the stabilizers of the invention, based on the weight of the polymer, but the most effective range will vary with the type of polymer: viz. 0.01% to 2.0%, preferably 0.02% to 1.0%, by weight for olefin, diene and styrene polymers; 0.01% to 1.0%, preferably 0.02% to 0.5%, by weight for vinyl and vinylidene polymers; and 0.01% to 5.0%, preferably 0.02% to 2.0%, by weight for polyurethanes and polyamides. If desired, two or more of the stabilizers of the invention may be used together.

The stabilizers of the invention may readily be incorporated into organic polymers by conventional techniques at any convenient stage prior to the manufacture of shaped articles therefrom. For example, the stabilizer may be mixed with the polymer in dry powder form, or a suspension or emulsion of the stabilizer may be mixed with a solution, suspension or emulsion of the polymer.

The stabilized polymeric compositions of the present invention may optionally also contain one or more of various conventional additives, such as the following:

Antioxidants
Simple, 2,6-dialkylphenols, such as, for example, 2,6-di-t-butyl-4-methylphenol, 2-t-butyl-4,6-dimethylphenol, 2,6-di-t-butyl-4-methoxymethylphenol and 2,6-dioctadecyl-4-methylphenol.

Derivatives of alkylated hydroquinones, such as, for example, 2,5-di-t-butylhydroquinone, 2,5-di-t-amylhydroquinone, 2,6-di-t-butylhydroquinone, 2,5-di-t-butyl-4-hydroxyanisole, 3,5-di-t-butyl-4-hydroxyanisole, tris(3,5-di-t-butyl-4-hydroxyphenyl)phosphite, 3,5-di-t-butyl-4-hydroxyphenylstearate and di-(3,5-di-t-butyl-4-hydroxyphenyl)adipate.

Hydroxylated thiodiphenyl ethers, such as, for example, 2,2'-thiobis(6-t-butyl-4-methylphenol), 2,2'-thiobis(4-octylphenol), 4,4'-thiobis(6-t-butyl-3-methylphenol), 4,4'-thiobis(3,6-di-s-amylphenol), 4,4'-thiobis(6-t-butyl-2-methylphenol) and 4,4'-bis(2,6-dimethyl-4-hydroxyphenyl)disulphide.

Alkylidene-bisphenols, such as, for example, 2,2'-methylene-bis(6-t-butyl-4-methylphenol), 2,2'-methylene-bis(6-t-butyl-4-ethylphenol), 4,4'-methylene-bis(6-t-butyl-2-methylphenol), 4,4'-methylene-bis(2,6-di-t-butylphenol), 2,6-di-(3-t-butyl-5-methyl-2-hydroxybenzyl)-4-methylphenol, 2,2'-methylene-bis[4-methyl-6-(α- methylcyclohexyl)phenol], 1,1-bis[3,5-dimethyl-2-hydroxyphenyl]butane, 1,1-bis(5-t-butyl-4-hydroxy-2-methylphenyl)butane, 2,2-bis(5-t-butyl-4-hydroxy-2-methylphenyl)butane, 2,2-bis(3,5-di-t-butyl-4-hydroxyphenyl)propane, 1,1,3-tris(5-t-butyl-4-hydroxy-2-methylphenyl)butane, 2,2-bis(5-t-butyl-4-hydroxy-2-methylphenyl)-4-n-dodecylmercaptobutane, 1,1,5,5-tetra(5-t-butyl-4-hydroxy-2-methylphenyl)pentane and ethylene glycol bis[3,3-bis(3'-t-butyl-4'-hydroxyphenyl)butyrate].

O-, N- and S-benzyl compounds, such as, for example 3,5,3',5'-tetra-t-butyl-4,4'-dihydroxydibenzyl ether, 4-hydroxy-3,5-dimethylbenzyl-mercaptoacetic acid octadecyl ester, tri(3,5-di-t-butyl-4-hydroxybenzyl)amine, and bis(4-t-butyl-3-hydroxy-2,6-dimethylbenzyl)dithiolterephthalate.

Hydroxybenzylated malonic esters, such as, for example, 2,2-bis(3,5-di-t-butyl-2-hydroxybenzyl)malonic acid dioctadecyl ester, 2-(3-t-butyl-4-hydroxy-5-methylbenzyl)malonic acid dioctadecyl ester, 2,2-bis(3,5-di-t-butyl-4-hydroxybenzyl)malonic acid di-dodecylmercaptoethyl ester, and 2,2-bis(3,5-di-t-butyl-4-hydroxybenzyl)malonic acid di(4-t-octylphenyl)ester.

Hydroxybenzyl aromatics, such as, for example, 1,3,5-tri(3,5-di-t-butyl-4-hydroxybenzyl)-2,4,6-trimethylbenzene, 1,4-di(3,5-di-t-butyl-4-hydroxybenzyl)-2,3,5,6-tetramethylbenzene, and 2,4,6-tri(3,5-di-t-butyl-4-hydroxybenzyl)phenol.

s-Triazine compounds, such as, for example, 2,4-bisoctylmercapto-6-(3,5-di-t-butyl-4-hydroxyanilino)-s-triazine, 2-octylmercapto-4,6-bis(3,5-di-t-butyl-4-hydroxyanilino)-s-triazine, 2-octylmercapto-4,6-bis(3,5-di-t-butyl-4-hydroxyphenoxy)-s-triazine, 2,4,6-tris(3,5-di-t-butyl-4-hydroxyphenoxy)-s-triazine, 2,4,6-tris(3,5-di-t-butyl-4-hydroxyphenylethyl)-s-triazine, and 1,3,5-tris(3,5-di-t-butyl-4-hydroxybenzyl)isocyanurate.

Amides of 3,5-di-t-butyl-4-hydroxyphenylpropionic acid, such as, for example, 1,3,5-tris(3,5-di-t-butyl-4-hydroxyphenyl-propionyl)-hexahydro-s-triazine, and N,N'-bis(3,5-di-t-butyl-4-hydroxyphenylpropionyl)hexamethylenediamine.

Esters of 3,5-di-t-butyl-4-hydroxyphenylpropionic acid with monohydric or polyhydric alcohols, such as, for example, those with methanol, ethanol, octadecanol, 1,6-hexanediol, 1,9-nonanediol, ethylene glycol, 1,2-propanediol, diethylene glycol, thiodiethylene glycol, neopentyl glycol, pentaerythritol, 3-thiaundecanol, 3-thiapentadecanol, trimethylhexanediol, trimethylolethane, trimethylolpropane, trishydroxyethyl isocyanurate, and 4-hydroxymethyl-1-phospha-2,6,7-trioxabicyclo[2,2,2]octane.

Esters of 5-t-butyl-4-hydroxy-3-methylphenylpropionic acid with monohydric or polyhydric alcohols, such as, for example, those with methanol, ethanol, octadecanol, 1,6-hexanediol, 1,9-nonanediol, ethylene glycol, 1,2-propanediol, diethylene glycol, thiodiethylene glycol, neopentyl glycol, pentaerythritol, 3-thiaundecanol, 3-thiapentadecanol, trimethylhexanediol, trimethylolethane, trimethylolpropane, trishydroxyethyl isocyanurate, and 4-hydroxymethyl-1-phospha-2,6,7-trioxabicyclo[2,2,2]octane.

Esters of 3,5-di-t-butyl-4-hydroxyphenylacetic acid with monohydric or polyhydric alcohols, such as, for example, those with methanol, ethanol, octadecanol, 1,6-hexanediol, 1,9-nonanediol, ethylene glycol, 1,2-propanediol, diethylene glycol, thiodiethylene glycol, neopentyl glycol, pentaerythritol, 3-thiaundecanol, 3-thiapentadecanol, trimethylhexanediol, trimethyloleth-ane, trimethylolpropane, trishydroxyethyl isocyanurate, and 4-hydroxymethyl-1-phospha-2,6,7-trioxabicyclo[2,2,2]octane.

Acylaminophenols, such as, for example, N-(3,5-di-t-butyl-4-hydroxyphenyl)stearic acid amide and N,N'-bis(3,5-di-t-butyl-4-hydroxyphenyl)thiobisacetamide.

Benzylphosphonates, such as, for example, 3,5-di-t-butyl-4-hydroxybenzylphosphonic acid dimethyl ester, 3,5-di-t-butyl-4-hydroxybenzylphosphonic acid diethyl ester, 3,5-di-t-butyl-4-hydroxybenzylphosphonic acid dioctadecyl ester, and 5-t-butyl-4-hydroxy-3-methylbenzylphosphonic acid dioctadecyl ester.

Aminoaryl derivatives, such as, for example, phenyl-1-naphthylamine, phenyl-2-naphthylamine, N,N'-diphenyl-p-phenylenediamine, N,N'-di-2-naphthyl-p-phenylenediamine, N,N'-di-s-butyl-p-phenylenediamine, 6-ethoxy-2,2,4-trimethyl-1,2-dihydroquinoline, 6-dodecyl-2,2,4-trimethyl-1,2-dihydroquinoline, mono- and di-octyliminodibenzyl, and polymerized 2,2,4-trimethyl-1,2-dihydroquinoline.

UV-absorbers and light protection agents 2-(2'-Hydroxyphenyl)benztriazoles, such as, for example, the 5'-methyl, 3', 5'-di-t-butyl, 5'-t-butyl, 5'-(1,1,3,3-tetramethylbutyl), 5-chloro-3',5'-di-t-butyl, 5-chloro-3'-t-butyl-5'-methyl, 3'-s-butyl-5'-t-butyl, 3'-[α-methylbenzyl]-5'-methyl, 3'-[α-methylbenzyl]-5'-methyl-5-chloro, 4'-hydroxy, 4'-methoxy, 4'-octoxy, 3',5'-di-t-amyl, 3'-methyl-5'-carbomethoxyethyl and 5-chloro-3',5'-di-t-amyl derivatives.

2,4-Bis(2'-hydroxyphenyl)-6-alkyl-s-triazines, such as, for example, the 6-ethyl, 6-undecyl and 6-heptadecyl derivatives.

2-Hydroxybenzophenones, such as, for example, the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivatives.

1,3-Bis(2'-hydroxybenzoyl)benzenes, such as, for example, 1,3-bis(2'-hydroxy-4'-hexyloxybenzoyl)benzene, 1,3-bis(2'-hydroxy-4'-octoxybenzoyl)benzene and 1,3-bis(2'-hydroxy-4'-dodecyloxybenzoyl)benzene.

Esters of optionally substituted benzoic acids, such as, for example, phenyl salicylate, octylphenyl salicylate, dibenzoylresorcinol, bis(4-t-butylbenzoyl)resorcinol, benzoylresorcinol and 3,5-di-t-butyl-4-hydroxybenzoic acid 2,4-di-t-butylphenyl ester, octadecyl ester or 2-methyl-4,6-di-t-butylphenyl ester.

Acrylates, such as, for example, α-cyano-β,β-diphenylacrylic acid ethyl ester or iso-octyl ester, α-carbomethoxycinnamic acid methyl ester, α-cyano-β-methyl-p-methoxycinnamic acid methyl ester or butyl ester, and N-(β-carbomethoxyvinyl)-2-methylindoline.

Nickel compounds, for example, nickel complexes of 2,2'-thiobis(4-t-octylphenol), such as the 1:1 and 1:2 complexes, optionally with other ligands such as n-butylamine, triethanolamine or N-cyclohexyldiethanolamine; nickel complexes of bis(4-t-octylphenyl)-sulphone, such as the 2:1 complex, optionally with other ligands such as 2-ethylcaproic acid; nickel dibutyldithiocarbamate; nickel salts of 4-hydroxy-3,5-di-t-butylbenzylphosphonic acid monoalkyl esters, such as the methyl, ethyl or butyl ester; the nickel complex of 2-hydroxy-4-methylphenyl undecyl ketonoxime; and nickel 3,5-di-t-butyl-4-hydroxybenzoate.

Oxalic acid diamides, such as, for example, 4,4'-dioctyloxyoxanilide, 2,2'-dioctyloxy-5,5'-di-t-butyloxanilide, 2,2'-di-dodecyloxy-5,5'-di-t-butyloxanilide, 2-ethoxy-5-t-butyl-2'-ethyloxanilide, 2-ethoxy-2'-ethyloxanilide, N,N'-bis(3-dimethylaminopropyl)oxalamide, mixtures of o- and p-methoxy and o- and p-ethoxy-disubstituted oxanilides, and mixtures of 2-ethoxy-5-t-butyl-2'-ethyloxanilide with 2-ethoxy-2'-ethyl-5,4'-di-t-butyloxanilide.

Metal deactivators, such as, for example, oxanilide, isophthalic acid dihydrazide, sebacic acid bisphenylhydrazide, bisbenzylidene oxalic acid dihydrazide, N,N'-diacetyladipic acid dihydrazide, N,N'-bis-salicyloyloxalic acid dihydrazide, N,N'-bis-salicyloylhydrazine, and N,N'-bis-(3,5-di-t-butyl-4-hydroxyphenylpropionyl)hydrazine.

Phosphites, such as, for example, triphenyl phosphite, diphenyl alkyl phosphites, phenyl dialkyl phosphites, trinonyl phenyl phosphite, trilauryl phosphite, trioctadecyl phosphite, 3,9-di-isodecyloxy-2,4,8,10-tetraoxa-3,9-diphosphaspiro[5,5]undecane, and tris(4-hydroxy-3,5-di-t-butylphenyl)phosphite.

Peroxide deactivators, such as, for example, esters of β-thiodipropionic acid (e.g., the lauryl, stearyl, myristyl and tridecyl esters), salts of 2-mercaptobenzimidazole (e.g., the zinc salt), and diphenylthiourea.

Polyamide stabilizers, such as, for example, copper salts in combination with iodides and/or phosphorus compounds and salts of divalent manganese.

Basic co-stablizers, such as, for example, polyvinyl-pyrrolidone, melamine, benzoguanamine, triallyl cyanurate, dicyandiamide, urea derivatives, hydrazine derivatives, amines, polyamides, polyurethanes, and alkali metal salts and alkaline earth metal salts of higher saturated or unsaturated fatty acids, (e.g., Ca stearate, Mg laurate, Na ricinoleate, K palmitate and Zn stearate).

PVC stabilizers, such as, for example, organic tin compounds, organic lead compounds and Ba/Cd salts of fatty acids.

Nucleating agents, such as, for example, 4-t-butylbenzoic acid, adipic acid, and diphenylacetic acid.

Other additives, such as, for example, plasticizers, lubricants (e.g., glycerol monostearate), emulsifiers, antistatic agents, flameproofing agents, pigments, carbon black, asbestos, glass fibre, kaolin and talc.

The use of the stabilizers of formula (I) with the above-listed antioxidants is particularly effective for the stabilization of olefin polymers.

The invention is further illustrated by the following non-limiting Preparations and Examples, in which all parts and percentages are by weight. Preparations A to D illustrate the preparation of the starting materials used to prepare the piperidine derivatives of the present invention, whilst Examples 1 to 10 illustrate the preparation of the piperidine derivatives themselves and Example 11 illustrates the stabilization of synthetic polymers using the piperidine derivatives. Throughout the Examples, the compounds of the invention are identified by means of the numbers appended to them in the list given hereinbefore.

PREPARATION A

2,6-diethyl-2,3,6-trimethyl-4-piperidone

To an ice-cooled mixture of 39.2 g of 2,4,6-triethyl-2,6-dimethyl-1,2,5,6-tetrahydropyrimidine and 18.0 g of methyl ethyl ketone were added 14.7 g of powdered calcium chloride dihydrate, followed by 3 ml of water. The resulting mixture was heated at 60° C, with stirring, for 15 hours, at the end of which time it was made alkaline by the addition of a 35% aqueous solution of sodium hydroxide and then extracted with diethyl ether. The ethereal solution was dried over potassium carbonate and the ether was evaporated off. The residue was distilled under reduced pressure to give 32.4 g. of 2,6-diethyl-2,3,6-trimethyl-4-piperidone (bp 91°-93° C/2.0 mmHg).

PREPARATION B

2,6-diethyl-2,3,6-trimethyl-4-piperidone 19.6 g of 2,4,6-triethyl-2,6-dimethyl-1,2,5,6-tetrahydropyrimidine and 0.4 g of ammonium bromide were added to 200 ml of methanol. Whilst maintaining the mixture at 10° C and stirring, 10 g of 37% hydrochloric acid were added dropwise. After completion of the addition, the resulting mixture was stirred at room temperature for 4 hours and there were then added dropwise 20 ml of 18% hydrochloric acid. The mixture was then heated at 30°-40° C for 7 hours and allowed to stand overnight at room temperature. After this, the mixture was made alkaline by the addition of a 40% aqueous solution of potassium carbonate, the methanol was evaporated off under reduced pressure, and the mixture was extracted with diethyl ether. The ethereal solution was dried over potassium carbonate and the diethyl ether was then removed. The residue was distilled under reduced pressure, giving 15.1 g of 2,6-diethyl-2,3,6-trimethyl-4-piperidone as an oil boiling at 91° – 93° C/2.0 mmHg.

PREPARATION C

2-ethyl-2,5-dimethyl-1-azaspiro[5.5]undecan-4-one 196.3 g of 2,4,6-triethyl-2,6-dimethyl-1,2,5,6-tetrahydropyrimidine were added dropwise to 300 ml of concentrated hydrochloric acid at 30° – 40° C, with stirring. When the addition was complete, the mixture was stirred for a further 4 – 5 hours and then neutralized with sodium carbonate and extracted with benzene. The resulting benzene solution was washed with, in turn, a 5% aqueous solution of sodium carbonate and water, and was then dried over potassium carbonate. After removal of benzene, the residue was distilled under reduced pressure, giving 72.4 g of 5-amino-5-methyl-3-heptanone (bp 46° – 48° C/2.5 mmHg).

14.3 g of the 5-amino-5-methyl-3-heptanone thus obtained were dissolved in 100 ml of methanol, and 10.0 g of cyclohexanone and 10.0 g of ammonium bromide were added to the resulting solution. Dry ammonia was then introduced into the solution at room temperature for 6 hours. The solution was then allowed to stand overnight, after which 10.0 g of potassium carbonate were added and the methanol was removed by evaporation under reduced pressure. The residue was extracted with benzene, and the benzene extract was washed with water and then dried over potassium carbonate. After removing the benzene, the residue was distilled under reduced pressure, giving 14.0 of 2,4-diethyl-4-methyl-1,5-diazaspiro[5.5]undec-1-ene (bp 93° – 94° C/1.5 mmHg).

11.1 g of the 2,4-diethyl-4-methyl-1,5-diazaspiro[5.5-]undec-1-ene and 2.5 g of ammonium bromide were dissolved in 70 ml of methanol, and 45 ml of water were added thereto, with stirring. The mixture was then stirred at room temperature for 8 hours. After removing the methanol by evaporation under reduced pressure, the residue was distilled under reduced pressure, giving 7.4 g of 2-ethyl-2,5-dimethyl-1-azaspiro[5.5]undecan-4-one, bp 119° – 122° C/1.5 mmHg.

PREPARATION D

3-allyl-2,2,6,6-tetramethyl-4-piperidone 154.7 g of 2,2,6,6-tetramethyl-4-piperidone, 160 g of piperidine and 10.0 g of p-toluenesulphonic acid monohydrate were dissolved in 200 ml of benzene. The solution was refluxed by heating for 8.5 hours, whilst the water formed in situ was removed by means of a Dean-Stark separator. The reaction mixture was then poured into a mixture of 700 ml of water, 200 ml of concentrated aqueous ammonia and 100 g of ice. The organic layer was separated, washed three times with water and then dried over magnesium sulphate. After removal of the solvent, the residue was distilled under reduced pressure, giving 46.6 g of 1,2,5,6-tetrahydro-2,2,6,6-tetramethyl-4-piperidinopyridine (bp 80° – 82° C/1 mmHg).

2.2 g of the 1,2,5,6-tetrahydro-2,2,6,6-tetramethyl-4-piperidinopyridine and 1.2 g of allyl bromide were dissolved in 3 ml of chloroform and the solution was then allowed to stand at room temperature for 24 hours. The crystals which precipitated were filtered off, washed with hexane and dissolved in 4 ml of concentrated aqueous ammonia; the resulting solution was extracted with hexane. The hexane extract was dried over potassium carbonate and, after removal of the hexane, 1.3 g of 5-allyl-1,2,5,6-tetrahydro-2,2,6,6-tetramethyl-4-piperidinopyridine were obtained. On thin layer chromatography using a 0.25 mm thick layer of alumina ("60F 254", available from Merck & Co.) and a mixture of benzene, hexane, ethyl acetate and triethylamine (2 : 2 : 1 : 0.5 by volume) as developing solvent, the compound showed a single spot with an Rf value of 0.80.

1.46 g of the 5-allyl-1,2,5,6-tetrahydro-2,2,6,6-tetramethyl-4-piperidinopyridine thus obtained were dissolved in a mixture of 3 ml of acetic acid, 1.5 g of sodium acetate and 3 ml of water, and the solution was allowed to stand overnight. To the solution were then added 6.0 g of sodium bicarbonate and 3 ml of concentrated aqueous ammonia; the solution was then extracted with hexane. The hexane extract was dried over magnesium sulphate and then treated with charcoal giving, after removal of the hexane, 0.91 g of 3-allyl-2,2,6,6-tetramethyl-4-piperidone. On thin layer chromatography using a 0.25 mm thick layer of alumina and a mixture of benzene, hexane, ethyl acetate and triethylamine (2 : 2 : 1 : 0.5 by volume) as developing solvent, the compound showed a single spot having an Rf value of 0.70.

EXAMPLE 1

7,9-diethyl-6,7,9-trimethyl-1,3,8-triazaspiro[4.5]decane-2,4-dione (Compound 1)

To a solution of 115 g of 2,6-diethyl-2,3,6-trimethyl-4-piperidone in 600 ml of 50% ethanol were added 168 g of ammonium carbonate and 57.8 g of potassium cyanide; the mixture was then heated at 60° – 70° C for 8 hours. The resulting mixture was then filtered and washed with water and cold methanol, after which the solvent was evaporated off, giving 78.0 g of Compound 1, mp 263° – 267° C (decomposition).

EXAMPLE 2

7,9-diethyl-3,6,7,9-tetramethyl-1,3,8-triazaspiro[4.5]-decane-2,4-dione (Compound 2)

To 40 ml of dimethylformamide were added 5.0 g of the potassium salt of 7,9-diethyl-6,7,9-trimethyl-1,3,8-triazaspiro[4.5]decane-2,4-dione (Compound 1) and 11.9 g of methyl iodide; the mixture was stirred at room temperature for 16 hours. The mixture was then poured into 150 g of ice water and extracted with benzene. The benzene extract was washed with ice water and then dried over potassium carbonate. After removing the benzene, the residue was chromatographed through a column of silica gel (eluent, ethyl acetate), giving 2.7 g of Compound 2, mp 137° – 142° C.

EXAMPLE 3

7,9-diethyl-6,7,9-trimethyl-3-phenyl-1,3,8-triazaspiro[4.5]decane-2,4-dione (Compound 14)

To a solution of 29.6 g of 2,6-diethyl-2,3,6-trimethyl-4-piperidone in 30 ml of ethanol were added 8.1 g of hydrogen cyanide. Whilst cooling the mixture to 0° – 5° C, a solution of 12 g of ammonia in 20 ml of ethanol was then added. The mixture was allowed to stand overnight at room temperature in a sealed tube and was then concentrated by evaporation under reduced pressure at a temperature below 25° C. 200 ml of diethyl ether were added to the residue and the mixture was dried over magnesium sulphate. The diethyl ether was removed from the mixture by evaporation under reduced pressure at a temperature below 25° C, giving 31.5 g of an oily product (crude 4-amino-4-cyano-2,6-diethyl-2,3,6-trimethylpiperidine), which showed an infra-red absorption at 2220 cm$^{-1}$, assigned to the cyano group.

7.2 g of the oily product were dissolved in 40 ml of benzene after which a solution of 4.3 g of phenyl isocyanate in 20 ml of benzene was added dropwise thereto at room temperature, with stirring. The mixture was stirred at room temperature for a further 3 hours and was then stirred for 3 hours at 40° – 50° C; after this, the mixture was allowed to stand overnight at room temperature. 200 ml of hexane were added to the reaction mixture, which caused crystals to precipitate. These crystals were separated by filtration and dried in vacuo, giving 7.2 g of 4-cyano-2,6-diethyl-2,3,6-trimethyl-4-(3-phenylureido)-piperidine, mp 167° – 170° C.

To 7.0 g of this crystalline product were added 20 ml of ethanol and 20 g of concentrated hydrochloric acid. The mixture was refluxed by heating for 10 hours, after which the ethanol was removed. 100 ml of water and 200 ml of ethyl acetate were added to the residue and then, with vigorous agitation, a saturated aqueous solution of sodium hydrogen carbonate was added at 5° – 15° C to adjust the pH of the aqueous layer to 8.0. The ethyl acetate layer was separated off, washed with water and then dried over magnesium sulfate. After removal of the solvent, the residue was first purified by column chromatography through silica gel (eluent: first, a 1 : 4 by volume mixture of benzene and ethyl acetate and then ethyl acetate alone) and then by preparative thin layer chromatography on a 2 mm thick layer of silica gel (Kieselgel 60F 254, available from Merck & Co.) using ethyl acetate as the developing solvent; 1.1 g of Compound 14, mp 150° – 153° C, were thus obtained.

EXAMPLE 4

7,9-diethyl-6,7,9-trimethyl-3-octyl-1,3,8-triazaspiro[4.5]decane-2,4-dione (Compound 5)

To 70 ml of dimethylformamide were added 8 g of the potassium salt of 7,9-diethyl-6,7,9-trimethyl-1,3,8-triazaspiro[4.5]decane-2,4-dione (Compound 1) and 5.2 g of octyl bromide; the mixture was heated, with stirring, at 60° C for 2 hours. The reaction mixture was then concentrated by evaporation under reduced pressure, and benzene was added to the residue. The resulting benzene solution was washed with water and then dried over magnesium sulphate. After removing the benzene, the resulting oily product was first purified by column chromatography on silica gel (eluent: benzene containing 5% of triethylamine) and then by recrystallization from hexane, giving 3.0 g of Compound 5, mp 65° − 67° C.

EXAMPLE 5

7,9-diethyl-3,6,7,8,9-pentamethyl-1,3,8-triazaspiro[4.5]-decane-2,4-dione (Compound 64)

To 5.5 g of the 7,9-diethyl-3,6,7,9-tetramethyl-1,3,8-triazaspiro[4.5]decane-2,4-dione (Compound 2) obtained in Example 2 were added 1.8 g of formic acid and 6.3 g of 37% formalin; the mixture was stirred at room temperature for one hour and then refluxed by heating for 5 hours. After cooling the reaction mixture, its pH was adjusted to a value of 8 by addition of a 5% aqueous solution of sodium hydrogen carbonate; the solution was then extracted with ethyl acetate. The extract was dried over potassium carbonate and the solvent was then removed. The residue was purified by column chromatography on silica gel (eluent: ethyl acetate) to give 5.58 g of Compound 64, mp 190° − 195° C.

EXAMPLE 6

7,9-diethyl-8-(2-hydroxyethyl)-6,7,9-trimethyl-3-octyl-1,3,8-triazaspiro[4.5]decane-2,4-dione (Compound 118)

To a solution of 6.0 g of 7,9-diethyl-6,7,9-trimethyl-3-octyl-1,3,8-triazaspiro[4.5]decane-2,4-dione (Compound 5) obtained as described in Example 4, in 40 ml of methanol were added 3 drops of concentrated hydrochloric acid and 3.5 g of ethylene oxide. The mixture was heated at 110° C for 24 hours in a sealed tube and then concentrated to give 6.5 g of Compound 118 as an oil. This product had an Rf value of 0.33 on thin layer chromatography on a 0.25 mm thick layer of silica gel (Kieselgel 60F 254, available from Merck & Co.; eluent, benzene containing 5% of triethylamine).

EXAMPLE 7

8-(2-benzoyloxyethyl)-7,9-diethyl-6,7,9-trimethyl-3-octyl-1,3,8-triazaspiro[4.5]decane-2,4-dione (Compound 130)

To a solution of 2.5 g of the oily product obtained in Example 6 in 30 ml of benzene were added 1.2 g of triethylamine; 0.8 g of benzoyl chloride was then added dropwise with ice-cooling. The mixture was refluxed by heating for 2 hours and, after cooling, an aqueous solution of potassium carbonate was added. The mixture was extracted with benzene. The extract was washed with water, dried over anhydrous sodium sulphate and then concentrated by evaporation under reduced pressure. The resulting oily product was first purified by column chromatography on silica gel (eluent: a 10 : 0.5 by volume mixture of hexane and triethylamine) and then by recrystallization from diethyl ether, giving 1.5 g of Compound 130 as crystals melting at 123° − 124.5° C.

EXAMPLE 8 p-bis(7,9-diethyl-6,7,9-trimethyl-2,4-dioxo-1,3,8-triazaspiro[4.5]dec-3-ylmethyl)benzene (Compound 43)

To 80 ml of dimethylformamide were added 8.0 g of the potassium salt of 7,9-diethyl-6,7,9-trimethyl-1,3,8-triazaspiro[4.5]decane-2,4-dione and 3.1 g of α,α'-dibromo-p-xylene; the mixture was heated, with stirring, at 60° C for 3 hours. The mixture was then concentrated by evaporation under reduced pressure and the residue was dissolved in chloroform. The chloroform solution was washed with water and dried over magnesium sulphate; the chloroform was then removed. The residue was purified first by column chromatography on silica gel (eluent: a 6 : 3 : 0.5 by volume mixture of ethyl acetate, benzene and triethylamine) and then by recrystallization from ethanol, giving 5.0 g of Compound 43 as crystals melting at 272° − 274° C.

EXAMPLE 9 p-bis(8-benzyl-7,9-diethyl-6,7,9-trimethyl-2,4-dioxo-1,3,8-triazaspiro[4.5]dec-3-ylmethyl)benzene (Compound 107)

To a solution of 1.0 g of Compound 43, obtained as described in Example 8, in 1 ml of dimethylformamide were added 1.0 g of triethylamine and 3.0 g of benzyl bromide; the mixture was heated at 150° C for 10 hours. An aqueous solution of potassium carbonate was then added and the mixture was extracted with chloroform. The chloroform extract was washed with water and then dried over magnesium sulphate. After removing the chloroform, the residue was purified first by preparative thin layer chromatography on a 2 mm thick layer of silica gel (Kieselgel 60F 254, available from Merck & Co.) using as eluent a 5 : 5 : 0.5 by volume mixture of benzene, ethyl acetate and triethylamine, and then by column chromatography on silica gel using chloroform as the eluent, giving Compound 107 and α-(7,9-diethyl-6,7,9-trimethyl-2,4-dioxo-1,3,8-triazaspiro[4.5]dec-3-yl)-α'-(8-benzyl-7,9-diethyl-6,7,9-trimethyl-2,4-dioxo-1,3,8-triazaspiro[4.5]dec-3-yl)-p-xylene as crystals. Compound 107 had a melting point of 277° − 280° C after recrystallization from ethanol.

EXAMPLE 10

7,9-diethyl-1,3,6,7,8,9-hexamethyl-1,3,8-triazaspiro[4.5]decane-2,4-dione (Compound 136)

To a solution of 2.95 g of Compound 64, obtained as described in Example 5, in 10 ml of dimethylformamide was added 0.67 g of 52.9% sodium hydride; the mixture was stirred overnight at room temperature. 2.26 g of methyl iodide were then added and the mixture was heated at 100° C for 15 hours, with stirring. After cooling the mixture, 100 ml of ice-water and 20 ml of a 20% aqueous potassium carbonate solution were added in turn; the mixture was then extracted with ethyl acetate. The extract was washed with water and dried over potassium carbonate. After removing the solvent from the extract, the residue was purified by column chromatography on silica gel (eluent: chloroform containing 2.5% of methanol), giving 2.9 g of Compound 136 as a white powder melting at 77° − 88° C.

The following compounds were prepared according to the procedures described in Examples 1 to 10.

3-butyl-7,9-diethyl-6,7,9-trimethyl-1,3,8-triazaspiro[4.5]decane-2,4-dione (Compound 4)
  mp 62°–73° C 7,9-diethyl-6,7,9-trimethyl-3-stearyl-1,3,8-triazaspiro[4.5]decane-2,4-dione (Compound 6)
  mp 36°–41° C 3-allyl-7,9-diethyl-6,7,9-trimethyl-1,3,8-triazaspiro[4.5]-
decane-2,4-dione (Compound 7)
mp 102°–105° C
7,9-diethyl-6,7,9-trimethyl-3-(2-methyl-2-propenyl)-
1,3,8-triazaspiro[4.5]decane-2,4-dione (Compound 8)
mp 96°–99° C
3-cyclohexyl-7,9-diethyl-6,7,9-trimethyl-1,3,8-triazas-
piro[4.5]decane-2,4-dione (Compound 13)
TLC: $R_f=0.50$ (silica gel; chloroform:methanol=9:1 by volume)
3-(2,3-epoxypropyl)-7,9-diethyl-6,7,9-trimethyl-1,3,8-
triazaspiro[4.5]decane-2,4-dione (Compound 18)
mp 105°–106° C
3-ethoxycarbonylmethyl-7,9-diethyl-6,7,9-trimethyl-
1,3,8-triazaspiro[4.5]decane-2,4-dione (Compound 19)
mp 125°–128° C
7,9-diethyl-3-(2-hydroxyethyl)-6,7,9-trimethyl-1,3,8-
triazaspiro[4.5]decane-2,4-dione (Compound 22)
mp 120°–122° C
3-(2-acetoxyethyl)-7,9-diethyl-6,7,9-trimethyl-1,3,8-
triazaspiro[4.5]decane-2,4-dione (Compound 25)
mp 111°–114° C
7,9-diethyl-6,7,9-trimethyl-3-(2-stearoyloxyethyl)-1,3,8-
triazaspiro[4.5]decane-2,4-dione (Compound 27)
mp 48°–49° C
3-(2-benzoyloxyethyl)-7,9-diethyl-6,7,9-trimethyl-1,3,8-
triazaspiro[4.5]decane-2,4-dione (Compound 28)
mp 131°–135° C
7,9-diethyl-6,7,9-trimethyl-3-(2-phenoxyethyl)-1,3,8-
triazaspiro[4.5]decane-2,4-dione (Compound 37)
mp 103°–105° C
1,4-bis(7,9-diethyl-6,7,9-trimethyl-2,4-dioxo-1,3,8-
triazaspiro[4.5]dec-3-yl)butane (Compound 39)
mp 207°–209° C
1,6-bis(7,9-diethyl-6,7,9-trimethyl-2,4-dioxo-1,3,8-
triazaspiro[4.5]dec-3-yl)hexane (Compound 40)
mp 200°–204° C
di[2-(7,9-diethyl-6,7,9-trimethyl-2,4-dioxo-1,3,8-triazas-
piro[4.5]dec-3-yl)ethyl] ether (Compound 41)
mp 169°–171° C
1,3-bis(7,9-diethyl-6,7,9-trimethyl-2,4-dioxo-1,3,8-
triazaspiro[4.5]dec-3-yl)-4-methylbenzene (Compound 46)
TLC: $R_f=0.44$ (silica gel; chloroform:methanol=85:15 by volume)
di[p-(7,9-diethyl-6,7,9-trimethyl-2,4-dioxo-1,3,8-triazas-
piro[4.5]dec-3-yl)phenyl] ether (Compound 48)
TLC: $R_f=0.48$ (silica gel; chloroform:methanol=85:15 by volume)
bis[p-(7,9-diethyl-6,7,9-trimethyl-2,4-dioxo-1,3,8-
triazaspiro[4.5]dec-3-yl)phenyl] methane (Compound 49)
TLC=$R_f=0.46$ (silica gel; chloroform-methanol=85:15 1 by volume)
1,2-bis(7,9-diethyl-6,7,9-trimethyl-2,4-dioxo-1,3,8-
triazaspiro[4.5]dec-3-ylacetoxy)ethane (Compound 50)
mp 226°–231° C
bis[2-(7,9-diethyl-6,7,9-trimethyl-2,4-dioxo-1,3,8-
triazaspiro[4.5]dec-3-yl) ethyl] adipate (Compound 54)
mp 85°–90° C (decomposition)
7,9-diethyl-6,7,8,9-tetramethyl-1,3,8-triazaspiro[4.5]-
decane-2,4-dione (Compound 63)
mp 252° C (decomposition)
1,6-bis(7,9-diethyl-6,7,8,9-tetramethyl-2,4-dioxo-1,3,8-
triazaspiro[4.5]dec-3-yl)hexane (Compound 77)
mp 194°–196° C
p-bis(7,9-diethyl-6,7,8,9-tetramethyl-2,4-dioxo-1,3,8-
triazaspiro[4.5]dec-3-ylmethyl)benzene (Compound 78)
mp 260°–263° C (decomposition)
8-allyl-7,9-diethyl-6,7,9-trimethyl-1,3,8-triazaspiro[4.5]-
decane-2,4-dione (Compound 86)
mp 259°–261° C
8-allyl-3-butyl-7,9-diethyl-6,7,9-trimethyl-1,3,8-triazas-
piro[4.5]decane-2,4-dione (Compound 88)
mp 97°–105° C
8-benzyl-7,9-diethyl-6,7,9-trimethyl-1,3,8-triazas-
piro[4.5]decane-2,4-dione (Compound 98)
TLC: $R_f=0.76$ (silica gel; ethyl acetate)
8-(2-acetoxyethyl)-7,9-diethyl-6,7,9-trimethyl-3-octyl-
1,3,8-triazaspiro[4.5]decane-2,4-dione (Compound 122)
TLC:$R_f=0.47$ (silica gel; benzene:ethyl acetate:triethylamine = 10:1:0.5 by volume)
6-ethyl-7,9-dimethyl-7,9-dipropyl-1,3,8-triazaspiro[4.5]-
decane-2,4-dione (Compound 146)
TLC:$R_f=0.42$ (silica gel; ethyl acetate:hexane:triethylamine = 10:5:2 by volume)
3-benzyl-6-ethyl-7,9-dimethyl-7,9-dipropyl-1,3,8-
triazaspiro[4.5]decane-2,4-dione (Compound 147)
TLC:$R_f=0.74$ (silica gel; ethyl acetate:hexane:triethylamine = 10:5:2 by volume)
6-isobutyl-7,9-diisopentyl-7,9-dimethyl-1,3,8-triazas-
piro[4.5]decane-2,4-dione (Compound 148)
TLC:$R_f=0.39$ (silica gel; ethyl acetate:hexane:triethylamine = 10:5:2 by volume)
3-benzyl-6-isobutyl-7,9-diisopentyl-7,9-dimethyl-1,3,8-
triazaspiro[4.5]decane-2,4-dione (Compound 149)
TLC:$R_f=0.73$ (silica gel; ethyl acetate:hexane:triethylamine = 10:5:2 by volume)
9-ethyl-6,7,9-trimethyl-7-phenyl-1,3,8-triazaspiro[4.5]-
decane-2,4-dione (Compound 151)
mp 302° C (decomposition)
14-ethyl-6,14-dimethyl-1,3,13-triazadispiro[4.1.5.3]pen-
tadecane-2,4-dione (Compound 154)
mp 223°–226° C
3-butyl-14-ethyl-6,14-dimethyl-1,3,13-triazadis-
piro[4.1.5.3]pentadecane-2,4-dione (Compound 155)
mp 142°–146° C
6-allyl-7,7,9,9-tetramethyl-1,3,8-triazaspiro[4.5]decane-
2,4-dione (Compound 159)
mp < 300° C

EXAMPLE 11

Mixtures were made from 100 parts of unstabilized polypropylene (MFI about 20) and 0.25 part of each in turn of the stabilizers shown in the following Table. The resulting mixtures were blended, melted and moulded under heat and pressure into films of thickness 0.1 mm. Control sheets were also made, one of the controls containing no stabilizer and the other containing Tinuvin 327, a Trade Mark for 2-(2-hydroxy-3,5-di-t-butyl-phenyl)-5-chlorobenzo-1,2,3-triazole, sold by Ciba-Geigy AG.

The sheets thus formed were exposed to ultraviolet radiation at 45° C in the "Standard Fade-Meter Type FA-1", manufactured and sold by Toyo Rika Instruments, Japan, a modification of the Atlas Fade-O-Meter Type FDA-R, which meets the requirements of paragraph 3.8 of Japanese Industrial Standard 1044-L.

The time taken before the sheets became brittle was measured and the results were expressed as a ratio of the time required for the sheet to become brittle when a stabilizer was used to the time required for the sheet to become brittle in the absence of stabilizer. The results are shown in the following Table.

Table

| Stabilizer Compound No. | Ratio |
|---|---|
| 1 | 13.5 |
| 2 | 37.5 |
| 4 | 37.5 |
| 5 | 32 |
| 6 | 20 |
| 7 | 36.5 |
| 8 | 22 |
| 9 | 20.5 |
| 13 | 30 |
| 14 | 37.5 |
| 18 | 37.5 |
| 19 | 18.5 |
| 22 | 24 |
| 25 | 15.5 |
| 27 | 19 |
| 28 | 35.5 |
| 37 | 32 |
| 39 | 31.5 |
| 40 | 31 |
| 41 | 31 |
| 43 | 23.5 |
| 46 | 20 |
| 50 | 29.5 |
| 54 | 23.5 |
| 63 | 30 |
| 64 | 36.5 |
| 77 | 31 |
| 78 | 17 |
| 88 | 31.5 |
| 122 | 20 |
| 130 | 35.5 |
| 136 | 26.5 |
| 151 | 17.5 |
| 154 | 17 |
| none (control) | 1 |
| Tinuvin 327 (control) | 6.5 |

What is claimed is:

1. A piperidine compound having the formula (I):

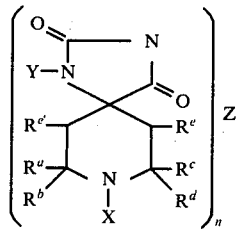

(I)

wherein
$R^a$ represents methyl group;
$R^b$ represents ethyl group;
$R^c$ represents an alkyl group of 1 to 5 carbons;
$R^d$ represents ethyl group;
or
$R^c$ and $R^d$, together with the carbon atom to which they are attached, represent a cycloalkyl group of 5 to 7 carbons;
one of $R^e$ and $R^{e'}$ represents hydrogen atom and the other of $R^e$ and $R^{e'}$ represents a lower alkyl group of 1 to 4 carbons or an allyl group;
$n$ is 1 or 2;
Y represents hydrogen atom or, when neither X nor Z represents hydrogen atom, Y represents hydrogen methyl group, ethyl group, allyl group or benzyl group;
X represents hydrogen atom, or an alkyl group of 1 to 4 carbons;
when $n = 1$:

Z represents hydrogen atom, an alkyl group of 1 to 18 carbons 2,3-epoxypropyl group, or phenyl group when $n = 2$:
X represents an alkylene group of 1 to 10 carbons and acid addition salts thereof wherein the acids are selected from the group consisting of sulphuric acid, hydrochloric acid or phosphoric acid; formic acid, acetic acid, valeric acid, stearic acid, oxalic acid, adipic acid, sebacic acid, maleic acid, benzoic acid, p-t-butylbenzoic acid, 4-hydroxy-3,5-di-t-butylbenzoic acid, salicylic acid or terephthalic acid; methanesulphonic acid or p-toluene-sulphonic acid; or phenylphosphonic acid.

2. A compound of claim 1 wherein
$R^a$ is methyl group;
$R^b$ and $R^d$ are each ethyl group;
$R^c$ is an alkyl group of 1 to 5 carbon atoms; or
$R^c$ and $R^d$, together with the carbon atom to which they are attached, form a cycloalkyl group having from 5 to 7 carbon atoms; one of $R^e$ and $R^{e'}$ is hydrogen atom and the other of $R^e$ and $R^{e'}$ is an alkyl group having from 1 to 4 carbon atoms or allyl group;
X is hydrogen or an alkyl group having 1 to 4 carbon atoms;
when $n$ is 1:
Z is hydrogen, an alkyl group of 1 to 18 carbon atoms, 2,3-epoxypropyl group or phenyl group;
when $n$ is 2:
Z is an alkylene group of 1 to 10 carbon atoms.

3. A piperidine compound according to claim 2, wherein
X represents hydrogen atom or methyl group;
Y represents hydrogen atom;
Z represents hydrogen atom, an alkyl group having from 1 to 8 carbon atoms, 2,3-epoxypropyl group, phenyl group; or
when $n = 2$:
Z represents an alkylene group having from 2 to 6 carbon atoms or p-xylylene group.

4. A polymer composition stabilized against photo- and thermal-deterioration thereof wherein there is incorporated, in an amount sufficient to prevent said deterioration, a piperidine of claim 1.

5. A polymer composition stabilized against photo- and thermal-deterioration thereof wherein there is incorporated, in an amount sufficient to prevent said deterioration, a piperidine of claim 2.

6. A polymer composition stabilized against photo- and thermal-deterioration thereof wherein there is incorporated, in an amount sufficient to prevent said deterioration, a piperidine of claim 3.

7. A polymer composition according to claim 4, wherein said piperidine derivative is selected from the group consisting of:
7,9-diethyl-3,6,7,9-tetramethyl-1,3,8-triazaspiro[4.5]-decane-2,4-dione
3-butyl-7,9-diethyl-6,7,9-trimethyl-1,3,8-triazaspiro[4.5]decane-2,4-dione
7,9-diethyl-6,7,9-trimethyl-3-octyl-1,3,8-triazaspiro[4.5]decane-2,4-dione
7,9-diethyl-6,7,9-trimethyl-3-phenyl-1,3,8-triazaspiro[4.5]decane-2,4-dione
3-(2,3-epoxypropyl)-7,9-diethyl-6,7,9-trimethyl-1,3,8-triazaspiro[4.5]decane-2,4-dione
1,4-bis(7,9-diethyl-6,7,9-trimethyl-2,4-dioxo-1,3,8-triazaspiro[4.5]dec-3-yl)butane
1,6-bis(7,9-diethyl-6,7,9-trimethyl-2,4-dioxo-1,3,8-triazaspiro[4.5]dec-3-yl)hexane 1,2-bis(7,9-diethyl-6,7,9-trimethyl-2,4-dioxo-1,3,8-triazaspiro[4.5]dec-3-ylacetoxy)ethane 7,9-diethyl-6,7,8,9-tetramethyl-1,3,8-triazaspiro[4.5]decane-2,4-dione 7,9-diethyl-3,6,7,8,9-pentamethyl-1,3,8-triazaspiro[4.5]decane-2,4-dione 1,6-bis(7,9-diethyl-6,7,8,9-tetramethyl-2,4-dioxo-1,3,8-triazaspiro[4.5]dec-3-yl)hexane 7,9-diethyl-1,3,6,7,8,9-hexamethyl-1,3,8-triazaspiro[4.5]decane-2,4-dione.

8. A polymer composition according to claim 4, wherein said piperidine derivative is incorporated in an amount of from 0.01 to 5.0% by weight based upon the weight of the polymer.

9. A polymer composition according to claim 7, wherein said piperidine derivative is incorporated in an amount of from 0.01 to 5.0% by weight based upon the weight of the polymer.

10. A polymer composition according to claim 4, wherein said polymer is polyvinyl chloride.

11. A polymer composition according to claim 4, wherein said polymer is a polyolefin.

12. A polymer composition according to claim 4, wherein said polymer is a polyurethane.

13. A polymer composition according to claim 4, wherein said polymer is a polyamide.

14. A polymer composition according to claim 4, wherein said polymer is a polypropylene.

* * * * *